US005681568A

United States Patent [19]

Goldin et al.

[11] Patent Number: 5,681,568
[45] Date of Patent: Oct. 28, 1997

[54] DEVICE FOR DELIVERY OF SUBSTANCES AND METHODS OF USE THEREOF

[75] Inventors: Stanley M. Goldin, Lexington; Nagesh K. Mahanthappa, Cambridge; Judith Sudhalter, Newton Lower Falls, all of Mass.; Eric Fine, Lausanne, Switzerland

[73] Assignee: Cambridge NeuroScience, Inc., Cambridge, Mass.

[21] Appl. No.: 293,465

[22] Filed: Aug. 19, 1994

[51] Int. Cl.⁶ ............... B29C 65/00; B29D 7/00; A61F 2/00; A61F 13/00; A61K 38/24; A61K 9/22; A61K 9/24; C07K 1/00

[52] U.S. Cl. ............ 424/184.1; 424/423; 424/468; 424/422; 424/424; 424/472; 424/486 T; 424/443; 424/449; 424/DIG. 7; 514/2; 514/12; 514/14; 264/41; 264/216; 530/399; 604/890 T

[58] Field of Search ............... 424/184.1, 423, 424/468, 472, 486 T, DIG. 7, 424, 443, 449; 264/41, 216; 604/890 T; 530/399; 514/2, 12, 14

[56] References Cited

U.S. PATENT DOCUMENTS

| | | | |
|---|---|---|---|
| 3,802,972 | 4/1974 | Fleischer | 156/7 |
| 3,883,626 | 5/1975 | Kamide | 264/49 |
| 3,962,414 | 6/1976 | Michaels | 424/19 |
| 4,032,309 | 6/1977 | Salemme | 55/158 |
| 4,066,512 | 1/1978 | Lai et al. | 195/127 |
| 4,164,560 | 8/1979 | Folkman et al. | 424/22 |
| 4,245,506 | 1/1981 | Meiklejohn | 73/336 |
| 4,391,797 | 7/1983 | Folkman et al. | 424/19 |
| 4,450,198 | 5/1984 | Michaels et al. | 428/315.5 |
| 4,567,009 | 1/1986 | Badenhop | 363/28 |
| 4,591,496 | 5/1986 | Cohen et al. | 424/15 |
| 4,595,583 | 6/1986 | Eckenhoff et al. | 424/15 |
| 4,601,893 | 7/1986 | Cardinal | 424/15 |
| 4,702,840 | 10/1987 | Degen | 210/638 |
| 4,814,182 | 3/1989 | Graham et al. | 424/484 |
| 4,962,091 | 10/1990 | Eppstein et al. | 514/2 |
| 4,996,154 | 2/1991 | Gabriels, Jr. | 435/240.241 |
| 5,018,112 | 5/1991 | Deprince | 424/468 |
| 5,106,627 | 4/1992 | Aebischer et al. | 424/424 |
| 5,141,748 | 8/1992 | Rizzo et al. | 424/425 |
| 5,160,672 | 11/1992 | Sasaki et al. | 264/41 |
| 5,160,745 | 11/1992 | DeLuca et al. | 424/487 |
| 5,175,092 | 12/1992 | Gabriels, Jr. | 435/29 |
| 5,232,601 | 8/1993 | Chu et al. | 210/646 |
| 5,273,755 | 12/1993 | Venktrama et al. | 424/448 |
| 5,290,494 | 3/1994 | Coombes et al. | 264/41 |

FOREIGN PATENT DOCUMENTS 0 518 697  12/1992  European Pat. Off. .

OTHER PUBLICATIONS

Yamakawa et al., 1983, Controlled release of insulin from plasma-irradiated sandwitch device using poly-DL-lactic acid, Biol. Pharm. Bull. 16(2):182-187.

Kim et al., 1993, Controlled release of drugs from reservoir type devices coated with porous polyurethane membranes, J. Kor. Pharm. Sci., 23(4):207-211.

Aebischer, P. et al. (1989) *J. Neurosci. Res.* vol. 23, pp. 282-289.

Aebischer, P. Guenard, V. and Brace, S. (1989) *J. Neurosci.* vol. 9, pp. 3590-3595.

Madison, R.D. et a. (1983) *Brain Research* vol. 447, pp. 325-334.

Madison, R.D., Archibald, S J. and C. Kraup (1992) *Wound Healing: Biochemical and Clinical Aspects* edited by I.K. Cohen, F. Diegelman, and W.J. Lindblad; W.B. Saunders Co., Philadelphia, PA; pp. 450-487.

Marchionni. M. A. et al., *Nature* (1993) vol. 362, pp. 312-318.

Mahanthappa, N. et al. (1994) *Development* vol. 120, pp. 1373-1384.

Martin, G. R. and Timpl, R. (1987) *Ann. Rev. Cell Biol.* vol. 3, pp. 57-85.

Massague, J. and Pandiella, A. (1993) *Ann. Rev. Biochem.* vol. 62, pp. 515-541.

Advances in Controlled Release Technology: Polymeric Delivery Syustems for Drugs, Pesticides and Foods, (1994) Massachusetts Institute of Technology, Cambridge, MA, vol. I-II.

*Primary Examiner*—Paula K. Hutzell
*Assistant Examiner*—N. M. Minnifield
*Attorney, Agent, or Firm*—Gregory B. Butler; Christine C. O'Day

[57] ABSTRACT

This invention comprises devices and methods for producing a composite microporous membrane specifically tailored to be useful for optimizing the delivery of macromolecules to a therapeutic target.

20 Claims, 13 Drawing Sheets

Steps in the Creation of a CND Delivery Device Slow Release Membrane

Cross-section of CND Delivery Device

Microskin

Underlayment

Noncovalently immobilized and releasable macromolecule(s)

Comparison of rhGGF2 Release Rate From a CND Controlled Release Device
Formed on a Polysulfone Hollow Fiber Underlayment ("tube") with Release
from a Nonporous Collagen Film ("NPC") of the Prior Art

Mathematical Model of GGF Concentration Changes and Pseudo-Steady State [GGF] Resulting From GGF Release Into a Nerve Guide Tube

Consider a cylinder of radius R and length L.
The surface area of an Immobilon-C coating this cylinder is $2\pi RL$.

Also, consider a circular filter (*in-vitro* expt.) releasing GGF.

Radius of filter = r

Figure 3C

The formulae sought are:

Rate of release from filter per unit area = $Q_f = \dfrac{G}{\Pi r^2}$ (units of pmoles/ hr/ cm$^2$)

Where $G$ = release rate in pmoles/hr

Rate of release as a function of time = $Q(t)$ change in [GGF] in cylinder = $Q_v = Q_f *(2\Pi RL\ /\ \Pi R^2 L)$ $\qquad\qquad\qquad\qquad\qquad = Q_f *(2/R)$ (units of **pmoles/ mm$^3$*hr**)

Convert to pmolar, by changing mm$^3$ to liters: multiply above by $10^6$ mm$^3$/L

\*\*\*\*\*\*\*\*\*\*\*\*\*\*\*\*\*\*\*\*\*\*\*\*\*\*\*\*\*\*\*\*\*\*\*\*\*\*\*\*\*\*\*\*

$r = 2.5$ mm (filter)

$R = 0.7$ mm (nerve guide tube)

To create a meaningful but not overly complicated model:

d[GGF]/dt = $Q_v$ - k[GGF]  (rate of release minus rate of decay)

This is a differential equation of the form:

$\quad$ dy/dx = a -by

The integral that solves this is:

$\quad \int$ dy/(a-by) = $\int$ dx $\quad$ x = - 1/b [ln (a-by)]

Translating the above to our case:

$\quad$ t = [ln ($Q_v$ - k [GGF] ) ] / k

Then exponentiate:

when $Q_v = 0$, d[GGF] / dt = ( -0.693 / $\tau$ ) • [GGF] $\qquad$ *(equation 1)*

$\quad$ (where $\tau$ = half-life of disappearance of soluble GGF)

Equation 1 solves for the rate of decay of GGF at a given point in time as a function of GGF half-life in the nerve guide tube.

At steady state, d[GGF]/dt = $Q_v$ - k [GGF] = 0 so $Q_v$ = k [GGF]

From the above, k = 0.693/$\tau$

Solve $\qquad$ ----> [GGF] = $\tau$•$Q_v$ / 0.693 <-----

Alternate Configurations of CND Delivery Device Within a Nerve Guide Tube
Figure 5A
Lining nerve guide tube between cut ends
Figure 5B
Enlarged View
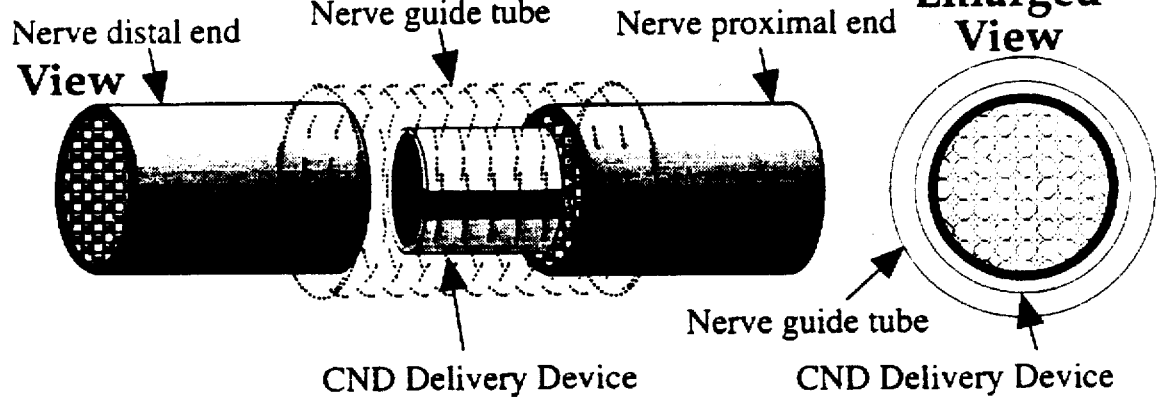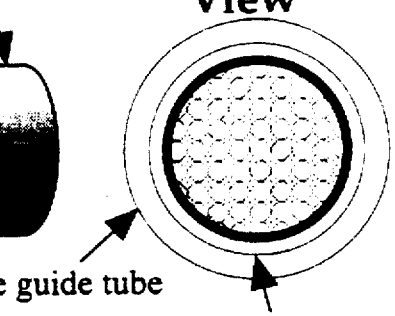
Figure 5C
Ribbon in center of nerve guide tube
Figure 5D
Enlarged View
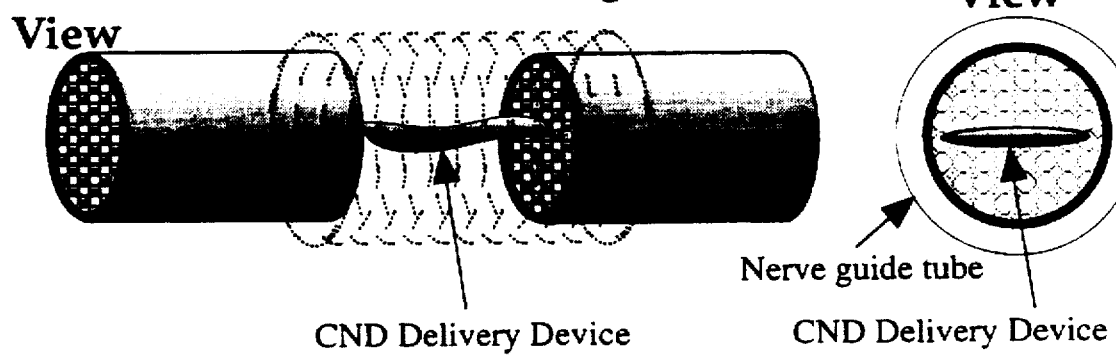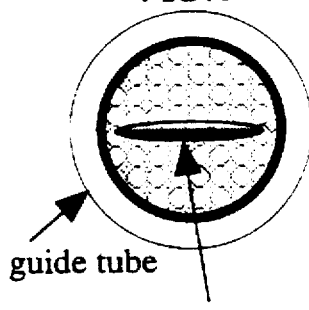
Figure 5E
Threadlike structure
Figure 5F
Enlarged View
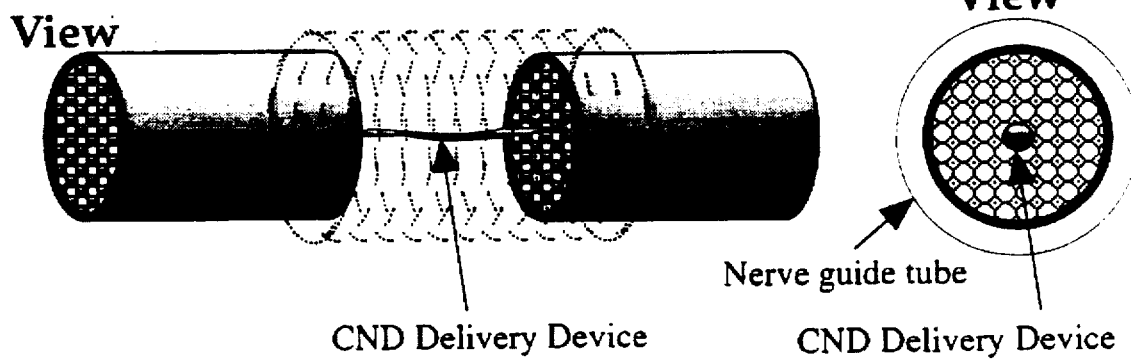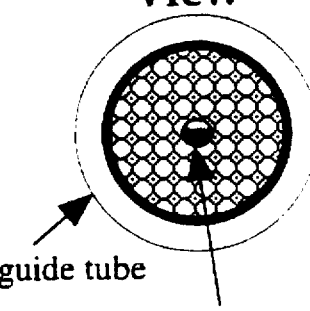

*In Vivo* Stability of rhGGF2 Activity

Each solid circle (o) denotes level of activity from a single GGF-treated animal.

Crosses (x) denote activity obtained from control animals.

GGF Concentration Dependence for Stimulation of Rat Schwann Cell DNA Synthesis

Sustained Release of GGF from a Collagen Microskin Coating a Cellulosic Underlayment Sustained Release of GGF from a Collagen Microskin Coating a Cellulosic Underlayment, Modeled as Rate of Increase in [GGF] Within Nerve Guide Tube

Figure 10

Predicted Decay of [GGF] in Prior Regeneration Experiment Based on Extrapolation of *In Vivo* Data

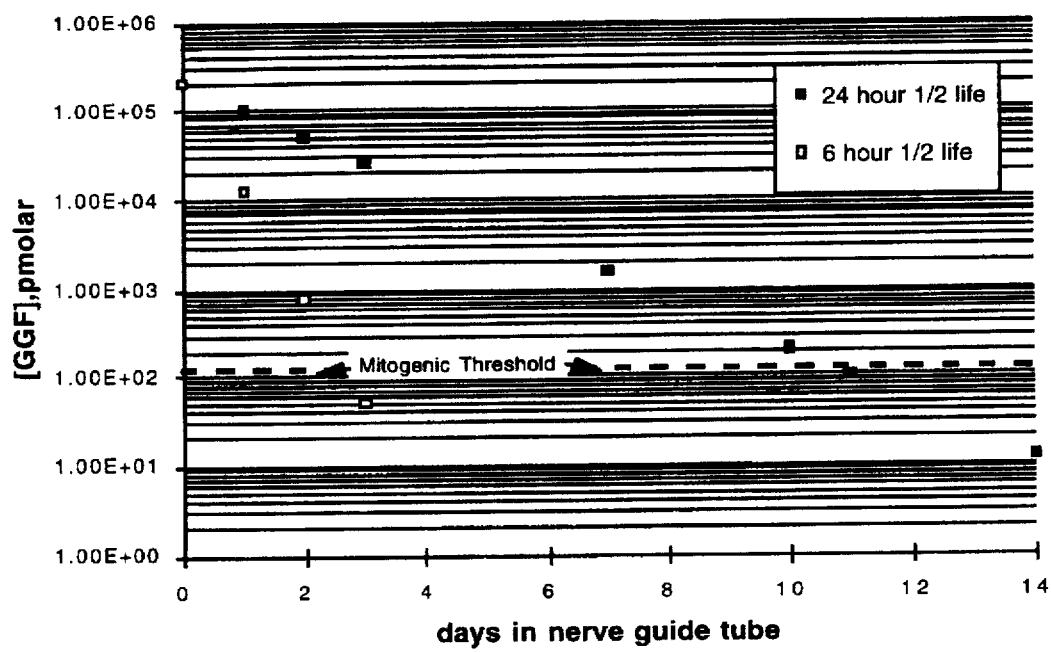

Conclusion:

A conclusion can be drawn that [GGF] will decay below the threshhold for stimulation of Schwann cells between 3 and 10 days, depending on the presumed half-life for GGF disappearance in the nerve guide tube (upper and lower estimates having been based on *in-vivo* experiments).

Sustained Release of bFGF from a Collagen Microskin Coating a Cellulosic Underlayment

DEVICE FOR DELIVERY OF SUBSTANCES AND METHODS OF USE THEREOF

BACKGROUND OF THE INVENTION

Description of Related Art

It has long been appreciated that controlled, sustained release of drugs or other therapeutic agents may enhance the efficacy and/or safety of the outcome of administration of said drug or therapeutic agent (for reviews, see Langer, R. S. (April, 1983) Drug Ther., 217–231 and Langer, R. and Peppas, N. A. (1992) BMES Bull. 16, 3–7). In the absence of administration of a therapeutic agent in a manner that affords controlled release, levels of said agent in the patient may oscillate substantially, at times reaching concentrations that could be toxic or produce undesirable side effects, and at other times falling below the levels required for therapeutic efficacy. A primary goal of the use of devices and/or methods for controlled release is to produce greater control over the systemic levels of therapeutic agents.

In certain circumstances, another desirable use of controlled release methods is to target the delivery of a therapeutic agent specifically to the tissue or site that can benefit from the presence of such an agent. For example, substances used for cancer chemotherapy are known to have undesirable and common systemic side effects (such as nausea and bone marrow depression) at therapeutic levels [Devita, V. T. (1987) in Harrison's Principles of Internal Medicine, 11th ed., Braunwald et al. eds, New York, McGraw-Hill, pp. 433–39], and this has given rise to efforts to target chemotherapeutic agents specifically to the site of the disorder, particularly in the case of solid malignant tumors [Tomlinson, E. (1987) Advanced Drug Deliv. Rev. 1, 87–198; Shin, S. U. (1991) Biotherapy 3, 43–53].

Several different classes of controlled release strategies have been developed, principally involving: (a) release by controlled diffusion; (b) release controlled by osmotic forces resulting in substrate swelling or osmosis-driven mechanical action; and (c) release limited by chemical control of the interaction of the agent with a substrate to which it is adsorbed or bound.

Release by controlled diffusion

Release by controlled diffusion may be accomplished by means of containment of the therapeutic agent within a substrate whose small pore size and/or tortuosity of diffusion path thereof limits the diffusion of said agent through the substrate (Langer, R. S. (April, 1983) Drug Ther., 217–...; Eckenhoff et al., U.S. Pat. No. 4,595,583; Venktrama et al., U.S. Pat. No. 5,273,755; Aebischer et al., U.S. Pat. No. 5,106,627; Deprince et al, U.S. Pat. No. 5,008,112; Cardinal, U.S. Pat. No. 4,601,893). The therapeutic agent can be incorporated within the diffusion-limiting substrate, or said agent can be contained within a reservoir and the substrate may form a barrier through which said agent must pass in order to enter the patient's biological fluids. Materials that have been used to fabricate diffusion-controlled slow release devices [Langer, R. S. (April, 1983) Drug Ther., 217–231 and Langer, R. and Peppas, N. A. (1992) BMES Bull. 16, 3–7] include the non-degradable polymers polydimethyl siloxane, ethylene-vinyl acetate copolymers [Cohen et al, U.S. Pat. No. 4,591,496; Folkman et al., U.S. Pat. No. 4,164,560] and hydroxylalkyl methacrylates.

In some instances, said devices may be used non-invasively, such as in the case of drug delivery by means of a transdermal patch; examples of this include sustained delivery of the anti-anginal agent nitroglycerin or scopolamine to prevent motion sickness [Brown, L., and Langer, R. (1988) Ann. Rev. Med. 39, 221]. In other instances, among them the release from the walls of cylindrical nerve guide tubes of trophic factors believed to aid nerve regeneration [Aebischer, P. et al. (1989) J. Neurcsci. Res. 23, 282], it may be desirable for such an implantable delivery device to slowly decompose in vivo. This would obviate the need for, and expense of, an additional surgical procedure to remove the implanted device. Towards that end, diffusion-controlled slow release devices have been fabricated from biodegradable polymers, among them lactic/glycolic acid copolymers [Coombes et al., U.S. Pat. No. 5,290,494; DeLuca et al., U.S. Pat. No. 5,160,745]. The geometries of devices that operate by this means include spheres of microscopic and macroscopic dimensions, cylinders, flat sheets, and hollow hemispheres [Langer, R., and Peppas, N. (1992) ibid. and (1983) J. Macromolec. Sci. 23, 61].

A disadvantage of the diffusion-controlled release method is that diffusion of a substance may provide only a limited duration of confinement of an agent within the substrate. Furthermore, the diffusion rate of said substance may be affected by parameters that are difficult to control, among them the viscosity of the surrounding fluid and the dimensional changes of the substrate due to swelling, or to chemical and/or enzymatic attack. Microporous membranes for release of proteins by controlled diffusion have been fabricated from ethylene vinyl acetate (EVA), and said membranes have been used in vivo in a manner which demonstrates their therapeutic potential [Langer, R. and Peppas, N. A. (1992) BMES Bull. 16, 3–7]. An advantage of this approach is that the membranes are fabricated in a manner that produces microscopic pores containing the protein of interest, affording a high release capacity. However, the EVA slow release methodology suffers from several potential drawbacks, among them:

a) The necessity of using large amounts of protein. The procedure for fabrication of this controlled release membrane entails addition of dry protein powder to a polymer solution in a solvent such as methylene chloride, such that the protein powder particles form pores in the polymer, as the solvent evaporates [Folkman et al., U.S. Pat. Nos. 4,164,560; 4,391,797]. The size of the pores is determined by the size of the protein powder particles, and in order to create a large number of pores a substantial volume ratio of protein powder to total membrane volume must be used. When the resulting device is used in vivo, this can result in excessive amounts of incorporation of releasable protein. In many cases, among them the delivery of trophic factors to the site of a regenerating nerve, it may be undesirable to allow the concentration of said factors to be too high, as this may generate undesirable biological responses. Another reason for limiting the total amount of the trophic factor incorporated into a slow release device is economic, relating to the high cost of producing and/or purifying said factors.

One way in which these concerns have been dealt with is by the use of a "carrier protein", such as serum albumin [Aebischer, P. et al. (1989) J. Neurosci. Res. 23, 282]. The biologically active protein or peptide is co-dissolved with a much greater quantity of such an "inert" carrier protein in aqueous solution, and lyophilized to form the protein powder. The carrier protein is responsible for the physical process of pore formation. However, a drawback to this approach is that the resulting membrane must release large quantities of said carrier protein in order to release the biologically active protein, and this may produce toxicity and/or an undesirable immune response.

b) Possible denaturation of the protein during the fabrication procedure. The procedure for fabrication of the controlled release device entails addition of the dry protein powder to the synthetic polymer dissolved in a suitable organic solvent such as methylene chloride. Both drying and solvent exposure can denature the protein, causing it to lose its therapeutically relevant biological activity. This is particularly likely to happen if small amounts of moisture are present in the protein powder, and/or if the protein contains a labile, sensitive biological activity. An alternative to this procedure [Cohen et al., U.S. Pat. No. 4,591,496] entails adding the dry protein powder to solvent-free polymer and subsequently compressing the mixture into the form of a membrane. Although this obviates the need for use of solvent, the protein powder must still be dried and this method is still limited in its applicability by the other aforementioned considerations.

Release by solvent swelling

This approach to controlled delivery of therapeutic agents entails use of a device that employs the osmotic forces of solvent activation to govern release. One mode of this prior art is to incorporate the therapeutic agent in a polymer system that initially does not permit diffusion of said agent. Upon implantation of the device, bodily fluid is slowly absorbed. The absorption swells the polymer and/or solvates protein particles within said polymer, enabling diffusion of the drug out of the device [Folkman et al., U.S. Pat. Nos. 4,164,560; 4,391,797]. The rate of swelling determines the release rate, and a disadvantage of this approach is that this swelling rate is difficult to control in a manner that allows a single device to be used for a multiplicity of applications. It is commonly necessary to reformulate the entire polymer system each time such a device is used for delivery of a different agent. Alternatively, as practiced by Alza Corp., osmotic forces can be used to exert force on an inner chamber as a result of osmotic expansion of an outer chamber, resulting in controlled delivery of the inner chamber's contents [Michaels, A. S. et al., U.S. Pat. No. 4,450,198].

Chemically controlled sustained release

Release by chemical control most commonly involves chemical cleavage from a substrate to which a therapeutic agent is immobilized, and/or by biodegradation of the polymer to which the agent is immobilized [Langer, R. S. (April, 1983) Drug Ther., 217–231 and Langer, R. and Peppas, N. A. (1992) BMES Bull. 16, 3–7]. A disadvantage of this method is that biodegradation and/or chemical cleavage may be difficult to reproducibly control in vivo, as it usually depends, in whole or in part, on the action of physiological enzymes that may be present in variable levels from patient to patient, or that vary within a patient as a function of time and/or of said patient's physiological state.

Another variant of release by chemical control termed herein "controlled noncovalent dissociation or 'CND'", relates to release resulting from dissociation of an agent that is bound temporarily by non-covalent binding of the agent to a substrate. It has recently been reported that single or multiple layer collagen films have proven useful for this purpose [Song, S-Z (1992) EPA 0 518 697 A2]. This method is particularly well suited for controlled release of proteins or peptides, which are macromolecules capable of forming multiple non covalent ionic, hydrophobic, and/or hydrogen bonds that afford stable but not permanent attachment of proteins to a suitable substrate.

One disadvantage of the prior art relating to release by CND is that the films that have been fabricated for this purpose are relatively non-porous. Accordingly, the capacity for immobilization and controlled release of a therapeutic agent is constrained by the limited amount of surface area for release of said agent which is in contact with the medium into which the agent is released. This problem has been recognized and attempts have been made to circumvent it by arranging said films in multiple layers [Song, S-Z (1992) EPA 0 518 697 A2].

Collagen films have been coated on the surface of microporous substrates [Lai, C. J. and Goldin, S. M. U.S. Pat. No. 4,066,512; Gabriels Jr., J. E., U.S. Pat. Nos. 4,996,154 and 5,175,092], and a variety of other microporous substrates have been fabricated for the purpose of immobilizing proteins and peptides [Matsudaira, P. (1987) J. Biol. Chem. 262, 10035; Patterson, S. D. et al. (1992) Anal. Biochem. 202, 193; Curch, G. M. and W. Gilbert (1984) Proc. Nat. Acad. Sci. USA 81, 1991; Product Literature for the Immobilon Product line, Millipore Corp.]. However, to date, methods have not been developed which employ devices possessing a high surface to volume ratio for the release of proteins and peptides. Such a device would be useful in the treatment of many diseases and disorders.

SUMMARY OF THE INVENTION

This invention relates to a device comprising a method for producing a composite microporous membrane specifically tailored for utility in optimizing the delivery of macromolecules to a therapeutic target by controlled noncovalent dissociation ("CND"). The resulting microporous CND controlled release membrane is termed a "CND Controlled Release Device". The CND Controlled Release Device consists of three components (refer to FIGS. 1A, 1A-1 through 1A-5, and 1B):

a) A microporous underlayment.

b) A microskin, which is bound to the internal surfaces of the underlayment. The microskin is specifically tailored to bind macromolecules (see component 'c' below) noncovalently by cooperative secondary bonds, and slowly release the macromolecules by controlled noncovalent dissociation (CND). The microskin is bound to the internal surfaces of the underlayment in a manner that allows the resulting composite structure to retain the microporous character provided by the underlayment.

c) One or more macromolecule(s) to be bound and released.

The resulting CND Controlled Release Device contains intercommunicating capillary pores that allow the transport of released macromolecules from within the structure to the external bodily fluids. Biological macromolecules that are released can exert beneficial therapeutic effects on target tissue.

A preferred embodiment entails implantation of the device at or near the target of the desired therapeutic effect. A device of this type can also be used for extracorporeal administration of therapeutic macromolecules.

The current practice entails the use of osmotic minipumps, microspheres, transdermal patches, bioerodable polymers, and membranes co-releasing therapeutic agents with carrier proteins. No prior art exists which uses a composite structure, as described above, for the controlled delivery of macromolecules. We demonstrate herein that the present invention is particularly well-suited for selective, controlled delivery of a number of macromolecules (e.g., delivery of trophic factors for nerve regeneration). Advantages of the present invention over the prior art are summarized in Table 1 on page 13 and discussed below. The advantages include:

a) Release of only the substance one wishes to deliver. In contrast, certain devices of the prior art employing microporous membranes, such as devices produced by the aforementioned EVA membrane fabrication method [Cohen et al., U.S. Pat. No. 4,591,496; Folkman et al., U.S. Pat. Nos. 4,164,560; 4,391,797], entail the use of carrier protein particles as substrates for pore formation. The biological activity one wishes to deliver in a controlled manner is incorporated into said protein particle, and released along with the carrier protein.

b) A high surface/volume ratio. In comparison to flat impermeable films of the prior art [Song, S-Z (1992) EPA 0 518 697 A2], the current invention has a much higher capacity for controlled release, due to the internal network of intercommunicating capillary pores (c.f. FIG. 1A): the resulting high surface to volume ratio affords a release capacity per unit of macroscopic face surface area of membrane that is, in preferred embodiments, one to several orders of magnitude higher than said impermeable films of the prior art. A further concomitant advantage is independent control of the porosity, biocompatibility, bioerodability, and delivery kinetics by controlling the properties of each of the two components (underlayment and microskin).

In further contrast to the prior art of CND from impermeable films [Song, S-Z (1992) EPA 0 518 697 A2], underlayment material of controlled pore size can be created and used to fabricate a device of optimal porosity, surface to volume ratio, and accessibility of the releasable macromolecule to biological material at or beyond the membrane's external surface (c.f FIGS. 1A, 1A-1 through 1A-5, and 1B). For example, the pore size of the resulting CND Controlled Release Device can be made small enough to exclude cells and/or bacteria from within said Device, and this is desirable for the reasons cited in (c) below.

c) Protection of the bound macromolecules from proteolysis, phagocytosis, and other biological processes which may alter and/or degrade said molecules. In contrast to said impermeable films, the bulk of the release capacity rests within the internal network of intercommunicating capillary pores. Thus, it is possible to decrease the pore size, so that the macromolecule's access and thereby contact with cell surfaces and concomitant cell mediated phagocytosis, endocytosis and/or related processes which may degrade the insolubilized protein and/or the microskin, and/or alter said protein's release kinetics, is limited.

d) The use with relatively minimal modification, of a single composite device to release a variety of proteins and/or peptides. In contrast to diffusion-controlled release devices, the kinetics of release by the microporous CND device are relatively less sensitive to the molecular weight of the protein of therapeutic interest. Because preferred embodiments of the CND Controlled Release Device and methods of use thereof employ membranes whose pore size is normally much greater than molecular dimensions, the kinetics of release are governed primarily by the strength and number of the reversible cooperative secondary bonds which immobilize said protein for CND. These bonds form in a largely nonspecific manner between the microskin of the device and the protein; as illustrated herein, proteins of differing molecular weight and structure nonetheless are releasable over a similarly desirable time course (generally days to weeks). Many diffusion-controlled release devices would necessitate a major reformulation of the product to achieve the same result.

e) Selective targeting of the therapeutic agent. Limitation of the toxicity associated with the macromolecules to be released results from selective delivery to the site of action in the amounts and at the time needed. While in practice, the temporal and spatial selectivity of the current invention may not be absolute, it is clearly an improvement over more conventional modes of delivery, as will be illustrated herein (c.f. Examples 1 through 4; FIG. 2).

f) Prevention of undesirable or excessive release of an agent resulting from catastrophic device failure. Devices that depend on physical confinement of an agent to control its release (e.g. an implantable osmotic minipump) rather than on release mediated by dissociation of chemical bonds between the substance and the substrate, can produce massive release of said agent if the device should rupture. If the agent is a protein or peptide that can cause toxicity if its levels in bodily fluids are too high, massive release could have serious or even life threatening consequences. An example of note is the hormone insulin, which can produce potentially lethal insulin shock if its levels in the blood are excessive [Larner, J. (1985) in *Goodman and Gilman's Pharmacological Basis of Therapeutics*, 7th Edition, New York, Mac Millan, p. 1502). In contrast, the current invention combines the high release capacity of a diffusion-controlled device with the safety inherent in a chemically controlled release system. Should the CND microporous membrane rupture or become fragmented, massive release will be prevented since the fragments will retain controlled release properties closely resembling those of the original membrane.

TABLE 1

Advantages of CND Controlled Release Device Compared with Prior Art of Controlled Release

| Method of controlled release | (a) Release of only the substance one wishes to deliver | (b) High surface to volume ratio for containment | (c) Protection of releasable material & substrate from access to cells & bacteria | (d) Use of the same device to release a variety of proteins and/or peptides | (e) Selective Targeting of therapeutic agent | (f) Protection against catastrophic device failure |
|---|---|---|---|---|---|---|
| CND membranes | YES | YES | YES | YES | YES | YES |
| impermeable films for CND | YES | NO | NO | YES | YES (Possible, if lower release | YES |

TABLE 1-continued

| | Advantages of CND Controlled Release Device Compared with Prior Art of Controlled Release | | | | | |
|---|---|---|---|---|---|---|
| Method of controlled release | (a) Release of only the substance one wishes to deliver | (b) High surface to volume ratio for containment | (c) Protection of releasable material & substrate from access to cells & bacteria | (d) Use of the same device to release a variety of proteins and/or peptides | (e) Selective Targeting of therapeutic agent | (f) Protection against catastrophic device failure |
| EVA & related microporous structures (meth. of Folkman et al) | NO | YES | YES | POSSIBLE (if protein resists solvent denaturation) | capacity suffices) YES | PARTIAL (if device should fragment, some pores will rupture) |
| Osmotic minipumps related osmotically-controlled devices | YES | N.A. (different mode of delivery control) | YES | YES | YES | NO |
| Conventional systemic administration | YES, but poor control over time course of availability | N.A. | N.A. | N.A. | NO | N.A. |

BRIEF DESCRIPTION OF THE DRAWINGS

FIGS. 1A, 1A-1 through 1A-5, and 1B comprise a schematic diagram of the steps involved in creation of, and resulting composition of, a CND Controlled Release Device; FIG. 1A represents an external view of the CND Controlled Release Device and FIGS. 1A-1 through 1A-5 show several enlarged views of an internal microcapillary pore; FIG. 1B presents a cross-sectional view of said Device.

FIG. 2 illustrates controlled release of rhGGF2 from a CND Controlled Release Device in vitro, formed using a polysulfone hollow fiber membrane as an underlayment; wherein it further compares the amount of rhGGF2 released from said Device with release obtained from an impermeable film akin to the prior art, demonstrating greatly prolonged and enhanced release by a Device of the current invention as compared with the prior art.

FIGS. 3A, 3B and 3C describe the geometry and calculations used in a mathematical model of the dynamic changes in the concentration of rhGGF2 resulting from the two competing processes of release of rhGGF2 from a CND Controlled Release Device lining a nerve guide tube, and the removal of rhGGF2 from said tube by degradation and/or other processes, where said model is used to predict the length of time that the [rhGGF2] would remain above the threshold for Schwann cell proliferation.

FIG. 4 illustrates the pseudo-steady state intraluminal [rhGGF2] released from a CND Controlled Release Device lining a nerve guide tube, as a function of time and rhGGF2 decay time constant, in relation to the threshold for Schwann cell proliferation denoted by the horizontal dashed line; wherein using the model illustrated in FIGS. 3A, 3B and 3C, it estimates the time period for which rhGGF2 will remain above the threshold for stimulation of Schwann cell proliferation.

FIGS. 5A through 5F illustrate the placement of various configurations of the CND Controlled Release Device within a cylindrical nerve guide tube for the purpose of aiding the regeneration of transected nerve; FIGS. 5A, 5C and 5E present three alternate configurations and FIGS. 5B, 5D and 5F correspond to enlarged cross-sectional views of each of the respective device configurations within the nerve guide tube.

FIG. 10 illustrates the pseudo-steady state intraluminal [rhGGF2] if it is initially injected as a bolus into a nerve guide tube, as a function of time and rhGGF2 decay time constant, in relation to the threshold for Schwann cell proliferation denoted by the horizontal dashed line; wherein using the model illustrated in FIGS. 3A, 3B and 3C it estimates the time period for which rhGGF2 will remain above the threshold for stimulation of Schwann cell proliferation, demonstrating that it is both substantially shorter and more dramatically affected by the decay time constant than is the case for rhGGF2 released from a CND Controlled Release Device, as illustrated in FIG. 2.

DETAILED DESCRIPTION OF THE INVENTION

Figure 1A:
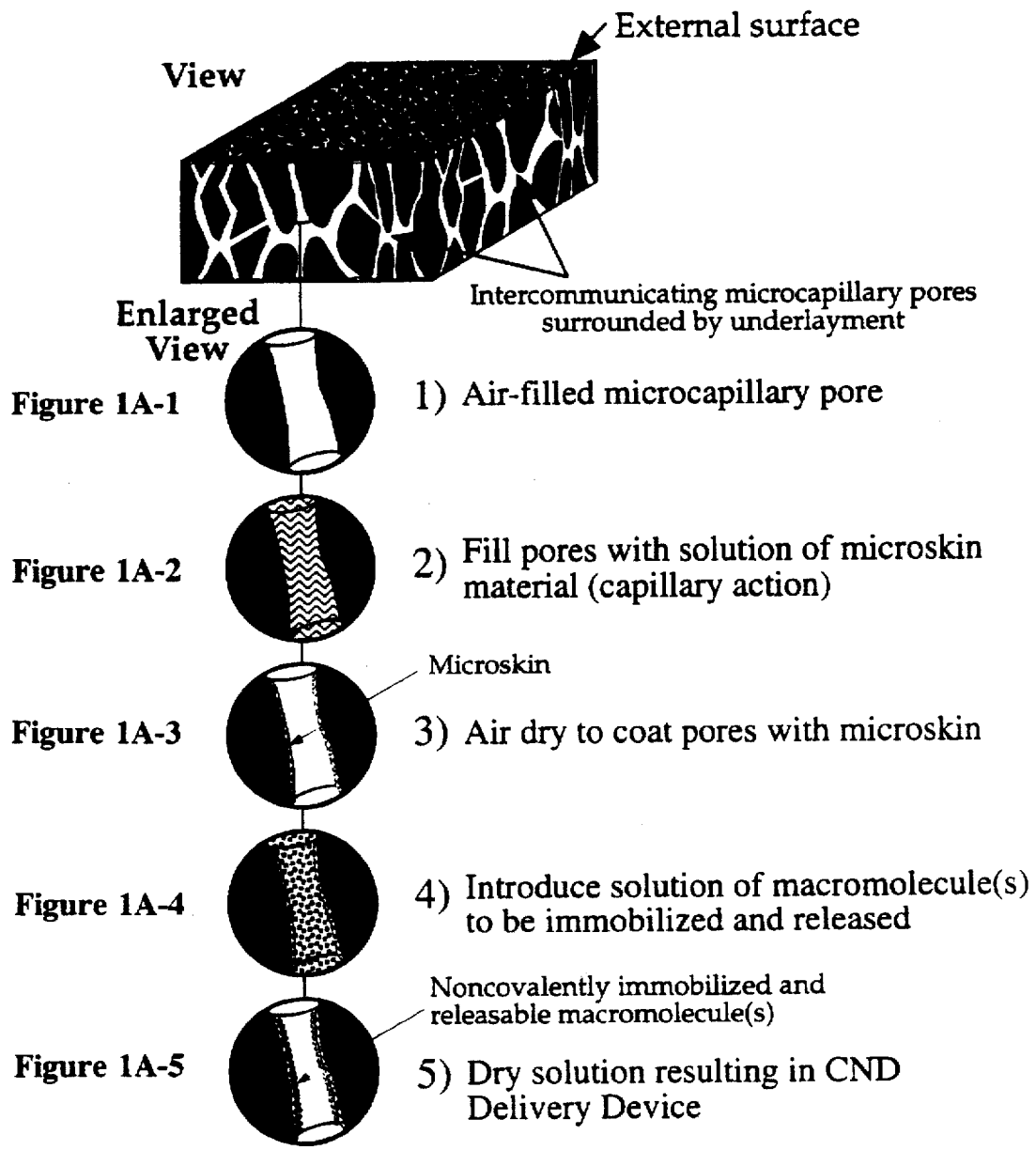
Figure 1B:
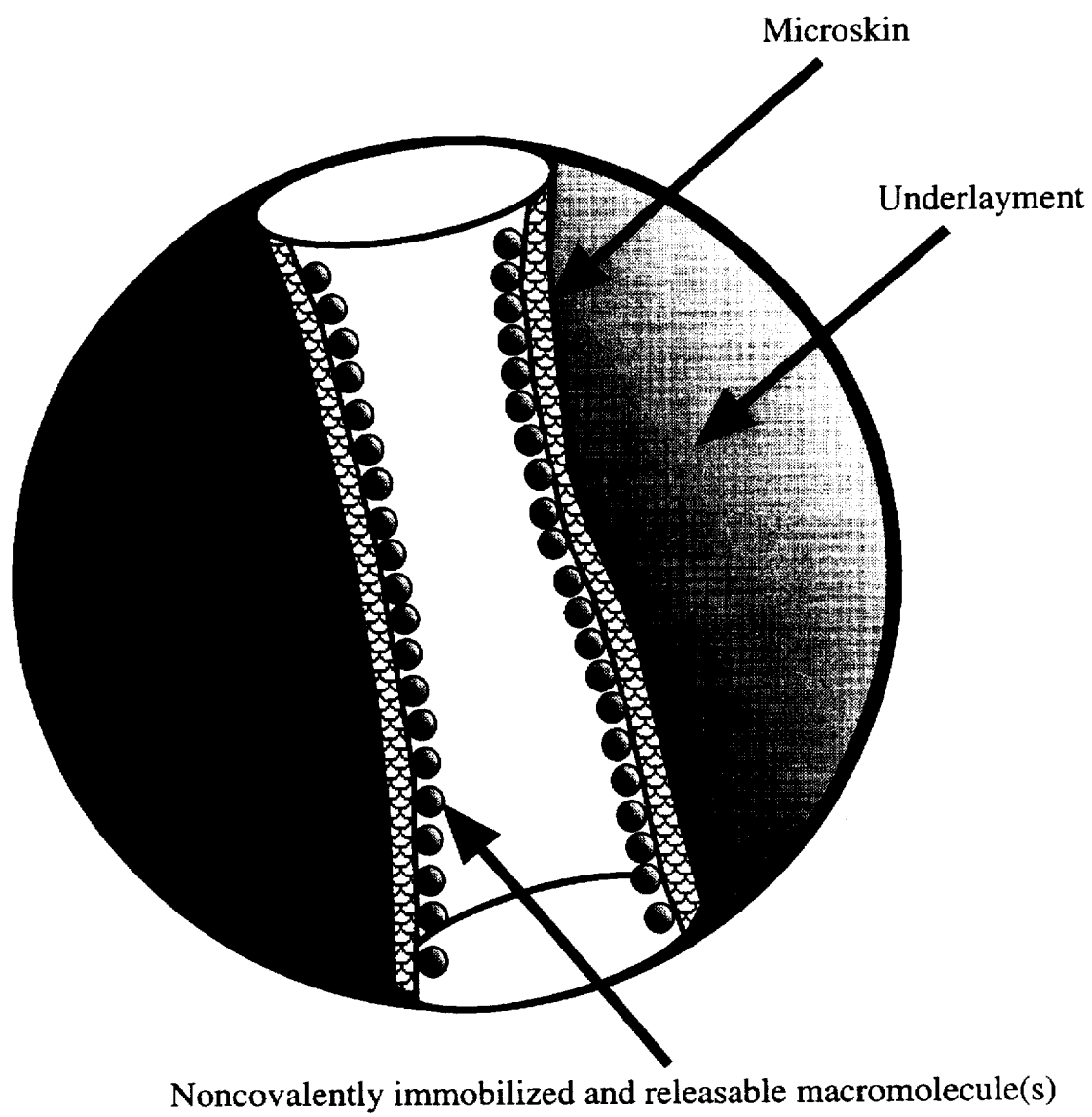

It is intended that all references cited shall be incorporated herein by reference.

I. DEFINITIONS OF KEY TERMS adhesive substance—a substance that tends to bind to another substance as a result of covalent and/or non-covalent chemical bonding and/or hydrophobic interactions and/or other molecular forces. As employed here, the property of being an adhesive substance is a desirable property for a microskin, because it enables it to stick to the interior surfaces defining the pores of an underlayment, as well as bind macromolecules for subsequent release.

biocompatible substance—a substance that, when implanted in or juxtaposed against a living body, or placed in contact with fluid or material actively leaving and re-entering said body, does not cause an adverse pathophysiological event that would raise significant concerns about the health of the individual.

biodegradable substance—as defined here, a substance that, when in a living body and/or in contact with a living body, will, over a period of time, disintegrate and/or decompose in a manner that alleviates the necessity for an invasive procedure for removal of said device. Biodegradation may result from active processes such as enzymatic means, or from spontaneous (e.g. non-enzymatic) processes, such as the chemical hydrolysis of ester bonds of polylactides that occurs at body temperature in an aqueous solution.

bound—a molecule or structure is said to be bound to another molecule or structure when they are linked through one or more covalent bonds, ionic bonds, hydrogen bonds, or hydrophobic interactions or other molecular forces in a stable manner. As defined here, two structures are also said to be "bound" as a result of physical constraints which cause said structures to remain juxtaposed against one another. For example, microporous TEFLON (poly-tetrafluoroethylene) may serve as a suitable underlayment for the current invention. A microskin such as a collagen coating may be said to be bound to the TEFLON underlayment even though one might argue that there is an absence or a minimum of intermolecular forces between TEFLON and collagen, and in such cases the main constraints result from collagen interacting with other collagen molecules which cause said collagen to surround structures making up the microporous network of the TEFLON, in a manner analogous to the way a rubber band or ribbon is bound to a package.

controlled delivery or release—as defined here, delivery of a substance by a device in a manner that affords control by said device over the rate and duration of exit of said substance from the device. For example, as described in the Background section of this application, delivery from controlled release devices can be controlled by diffusion out of said device, dissociation of chemical bonds, and the like.

cooperative non-covalent bonding—interactions between two or more molecules or substances that result from two or more non-covalent chemical bonds, among them hydrogen bonds, ionic bonds, hydrophobic interactions, or the like.

disorder—a disturbance of function and/or structure of a living organism, resulting from an external source, a genetic predisposition, a physical or chemical trauma, or a combination of the above, including but not limited to any mammalian disease.

environment of use—as defined here, the location in which a suitable embodiment of the current invention will be performing the function of controlled release. For example, said environment of use could be the eye, which would restrict the size and shape of the device to dimensions conforming with its placement that do not interfere with vision; or, the interior of a nerve guide tube, which would constrain it to conform to the dimensions of the tube in a manner that does not interfere with nerve regeneration.

macromolecule—as defined here, a molecule of molecular weight exceeding about 400 daltons. Examples of relatively small macromolecules include but are not limited to pentapeptides (i.e. a peptide of 5 amino acids), trisaccharides (a polysaccharide of 3 sugar monomer units), and any polymer containing 3 or more monomer units.

microskin—a thin layer of a substance, with one or more polymers as its main constituent(s), which binds to, and forms a thin coating upon, the surfaces defining the internal pores of the underlayment. Said microskin coats the underlayment in a manner that preserves the microporous character of the resulting composite structure, i.e. the microskin coats but does not completely fill the pores of the underlayment. This property preserves the ability of external fluids or gases to intercalate the porous network in a relatively unrestricted manner.

placement—as employed here, insertion and orientation of a device in a manner that allows it to produce the beneficial effect of controlled release without adversely affecting the target, individual, or environment of use.

polymer—a substance made up of covalently connected units, termed "monomers". Said monomers may be identical or dissimilar from one another. For example, a pentapeptide may be made of either identical or different amino acid monomer units (e.g. polylysine, or, in the case of the pentapeptide methionine enkephaline, its structure is tyrosine-glycine-glycine-phenylalanine-methionine, i.e. it is a polymer of non-identical amino acids).

protein—a polymer made up of three or more amino acids linked by peptide bonds. Generally, a protein of ten amino acids or less is referred to as a peptide. A protein may have other chemical constituents attached to it, e.g. sugars or lipids attached to it, but is still defined here as a protein: that is, for example, a glycoprotein or a lipoprotein is still referred to as a subclass of the general definition of proteins.

released—a molecule or structure is said to be released from another molecule or structure to which it was previously bound when they are no longer linked through one or more covalent, ionic, hydrogen, or hydrophobic bonds or other forces in a stable manner. Said structures are also said to be released from one another when the physical constraints (see definition of "bound") causing them to be bound to one another no longer constrain them to be juxtaposed against one another.

subject—as defined here, a mammal (particularly a human), or other organism such as an insect, bacterium, or a plant, that is the target of an agent delivered by a device of the invention.

sustained—as defined here, sustained release of a substance from a device of the current invention or a controlled delivery device of the prior art indicates that release occurs over a time period significantly exceeding the half-life for disappearance of the substance released, were it released as a single bolus by conventional means, e.g. by a single i.v. injection.

synthetic polymer—a polymer that comprises, in whole or in part, substances that are created by chemical synthesis, rather than produced naturally by an organism. A substance that is a natural occurring polymer may also be created by chemical synthesis, for example, peptides and nucleotides can be created either naturally or in the chemical laboratory.

therapy—the treatment of a disease or disorder by various methods. As employed here, said therapy includes controlled release of one or more therapeutically beneficial agents.

traumatic injury—an injury to a cell, tissue, or organism resulting from an adverse physical interaction with another object or force, for example an impact, scrape, cut, tear, or burn. A traumatic injury is distinguished from injuries resulting from other alterations of the environment such as hypoxia, chemical toxicity, or loss of blood supply to the cell, tissue or organism (i.e. ischemia).

treatment—as defined here, a procedure, e.g. a medical procedure, designed to exert the intended effect on the target of said treatment, that generally includes controlled release of a substance from a Device of the invention. Said treatment could have a beneficial effect on the target, such as may result from delivery of a trophic factor to aid nerve regeneration, or it could intentionally have an adverse effect, as the death of insects that are the target of controlled release of an insecticide.

trophic factor—a macromolecule, commonly but not exclusively a protein or peptide, that —as a result of its interaction with a target, affects in a measurable way the state of proliferation, differentiation, migration, growth, metabolism, or other growth-related property of said target or the organism or entity controlled by said target.

underlayment—a microporous structure of limited thickness (generally less than several mm) with one or more synthetic and/or biological polymers as its main constituent(s). Said underlayment provides dimensional stability, and a relatively high surface area per unit of volume due to its internal network of pores. Said pores are of dimensions ranging from about 100 Å to several hundred microns, and in current preferred embodiments range from about 1000 Å to 100 microns. Examples of suitable underlayments are membrane filters, depth filters, and NUCLEPORE filters (NUCLEPORE is a registered trademark of Corning Costar Corporation, 1 Alewife Center, Cambridge, Mass.).

II. DEVICES AND METHODS COMPRISING THE INVENTION

Devices may be constructed from a variety of materials and in a variety of configurations. The following sections describe alterative components and configurations of the present invention but are not intended to be limiting in any way.

A. Underlayment composition and fabrication methods

1. Membrane filter casting ("Millipore Filter method")

Microporous underlayments may be fabricated from a variety of polymeric materials by application of the methodology of membrane filter casting. Said casting methodology is well described in the literature [e.g., Badenhop, C. T., U.S. Pat. No. 4,569,009; Degen, P. J., et al., U.S. Pat. No. 4,702,840; Salemme, R. M., U.S. Pat. No. 4,032,309; Kamide, K., U.S. Pat. No. 3,883,626; and a variety of earlier references cited in these patents and has been used to produce membranes from variety of polymers, and for a variety of filtration applications. One of ordinary skill in the art should be readily able to fabricate underlayments by said methodology. In fact, as illustrated in Example 1, materials suitable for use as underlayments are commercially available as membrane filters from a number of suppliers (e.g., Millipore Corp., Bedford, Mass.; Amicon Corp., Bedford, Mass.; Gelman Sciences, Ann Arbor, Mich.). While not wishing to be limited by these examples, membrane filters of suitable composition have been made from the following materials: cellulose acetate; other cellulose esters, e.g. mixed esters of cellulose acetate and cellulose nitrate; nylon; polytetrafluoroethylene ("Teflon"); phenelynediamine-isophthalic acid copolymers; polycarbonate; polyvinylidene difluoride (PVDF); and polysulfones.

In brief, in an embodiment of this methodology, fabrication of underlayments by membrane filter casting involves the following steps. A suitable polymer is dissolved in a multi-component solvent system typically comprising organic solvents that differ in their volatility and their propensity to dissolve said polymer. The polymer solution is placed in a casting device, typically comprising a chemically inert chamber with a small slit at the bottom of said chamber through which the solution flows and/or is extruded. Said casting device is placed on a flat surface, and drawn at constant speed along the surface at a rate that enables a thin film of polymer solution (typically<2 mm thickness) to be deposited on said surface. Air or a gas such as nitrogen flows over the surface in a controlled manner; the more volatile solvents are initially the components that tend to evaporate most rapidly. As the composition of the solution changes the solubility limit of the polymer is reached and the polymer precipitates in a manner that results in an intercommunicating microporous network of hollow interstices. When solvent evaporation is complete, the resulting structure comprises the membrane filter for use as the underlayment of a CND Controlled Release Device.

As is generally known to one skilled in the art, the resulting pore size of the microporous network is controlled by varying the casting procedure. Casting variables that determine the pore size include but are not limited to: solvent composition, polymer composition, temperature of casting, and the rate of flow of air and/or other gases over the surface of the cast polymer solution. For use as the underlayment of a CND Controlled Release Device, while not wishing to be bound by these limits, suitable pore size as determined by the "bubble point" or "pore point" method [e.g., Badenhop, C. T., U.S. Pat. No. 4,569,009] may range from 500 Å to 10 µm. In this pore size range, particularly below ~3 µm, cells will be restricted from access to the interstices of the underlayment of a CND Controlled Release Device, preventing cell-mediated local damage, modification, or destruction of the device. This pore size range encompasses dimensions of the interstitial pore network that will minimally restrict the diffusion of released proteins and/or peptides. Thus it is the kinetics of CND that primarily control the rate of release of said macromolecules.

2. Hollow fiber/solution injection method (used to make Amicon hollow fibers)

Microporous underlayments may be fabricated from a variety of polymeric materials by application of the methodology of hollow fiber extrusion. Said hollow fiber fabrication methodology is well described in the literature [e.g., Chu, C. et al., U.S. Pat. No. 5,232,601; Nobuyoshi, K. et al., U.S. Pat. No. 5,160,672 and a variety of earlier references cited in these patents] and has been used to produce membranes from a variety of polymers, and for a variety of filtration and ultrafiltration applications. One of ordinary skill in the art should be readily able to fabricate underlayments by said methodology. In fact, as illustrated by the CND Controlled Release Device formed from hollow fibers as produced and used for trophic factor release (Example 4), materials suitable for use as hollow fiber underlayments are commercially available from a number of suppliers [e.g., W. R. Grace, Bedford, Mass.; Amicon Corp., Bedford, Mass.]. While not wishing to be limited by these examples, hollow fibers of suitable composition have been made from the following materials: cellulose acetate; other cellulose esters (e.g., mixed esters of cellulose acetate and cellulose); and polysulfones.

In brief, while not wishing to limit the scope of hollow fiber fabrication methodology that may be employed, fabrication of underlayments by hollow fiber extrusion commonly involve the following steps. A suitable polymer is dissolved in a multi-component solvent system typically comprising organic solvents that differ in their aqueous solubility, oil/water miscibility, and their propensity to dissolve said polymer. The polymer solution is placed in an extrusion device, typically comprising a chemically inert chamber through which fluid (commonly an aqueous solution) can continuously flow. One or more probes are positioned so that the outlet of the probe is below the surface of the flowing solution. Said probe consists of two concentric cylinders of differing diameters. The polymer solution is extruded through the annulus defined by the space between the inner and outer concentric cylinders, at constant speed and at a rate that enables a hollow microporous fiber of polymer to form as the polymer solution is extruded into the second solution in the large outer chamber. This results from the fact that the polymer is insoluble and hence rapidly precipitates in the form of a hollow fiber upon extrusion of the polymer solution. A solution is also commonly extruded through the hole defined by the inner surface of the inner cylinder; the purpose of this solution, in which said polymer solution is also insoluble, is to ensure that the polymer precipitates in the form of a fiber with a hollow core of defined diameter. By controlling the process parameters, among them solution composition, extrusion rates of the two solutions and temperature, the polymer precipitates in a manner that results in an intercommunicating microporous network of hollow interstices. The resulting structure, after some additional post processing to stabilize and wash the fiber, comprises the membrane filter for use as the underlayment of a CND Controlled Release Device.

As is generally known to one skilled in the art, the resulting pore size of the microporous network is controlled by varying the fabrication procedure. Variables that determine the pore size include but are not limited to: solvent composition, polymer composition, temperature of extrusion, and the rate of flow of one or more of the several solutions involved in the method. For use as the underlayment of a CND Controlled Release Device, while not wishing to be bound by these limits, suitable pore size as determined by the aforementioned "bubble point method" may range from 500 Å to 10 μm. In this pore size range, particularly below ~3 μm, cells will be restricted from access to the interstices of the underlayment of a CND Controlled Release Device, preventing cell-mediated local damage, modification, or destruction of the device. This pore size range encompasses dimensions of the interstitial pore network that will minimally restrict the diffusion of released proteins and/or peptides; thus it is the kinetics of CND that primarily control the rate of release of said macromolecules.

3. Microporous underlayments of ethylene vinyl acetate, polycarbonate, and related polymers Poly-ethylene vinyl acetate is one of several polymer systems that are currently know to be biocompatible and suitable for internal use, and as such constitute preferred embodiments for fabrication of microporous underlayments. Poly-ethylene vinyl acetate has been used in vivo as nerve guide tube material [Aebischer, P. et al. (1989) J. Neurosci. Res. 23, 282]. Underlayments can be made from poly-ethylene vinyl acetate and related polymers by known methods [e.g., Cohen et al., U.S. Pat. No. 4,591,496; Folkman et al., U.S. Pat. Nos. 4,164,560; 4,391,797], or by suitable modifications thereof. Upon membrane formation, the protein particles can be leached out by treatment with an enzyme solution, or suitable solvent, or by prolonged leaching from an aqueous solution. The microskin can then be formed upon the internal and external surfaces of this underlayment by one or more simple variants of the procedures described in Sections C and D below.

As an alterative means of fabrication of poly-ethylene vinyl acetate underlayments, said polymer system can be subjected to the membrane filter casting method described above. Upon dissolving poly-ethylene vinyl acetate in methylene chloride, suitable cosolvents and precipitating agents can be selected for formulation of a filter casting solution. By the semi-empirical process employed for optimization of the methodological details for filter casting in the past (optimization of solvent composition, temperature, air and/or drying agent flow rate, etc.), one skilled in the art should be readily able to formulate a microporous underlayment of suitable pore size by said method.

Underlayments can also be made by the procedure which produces so-called NUCLEPORE filters, first developed by General Electric Corp. [e.g. Meiklejohn, W. H., U.S. Pat. No. 4,245,506; Fleischer, R. L. (1974) U.S. Pat. No. 3,802, 972]. Briefly, a thin film made of polycarbonate or some other suitable polymer is subjected to neutron bombardment and controlled etching of the resulting holes, to produce cylindrical pores of controllable dimensions, typically 0.1 μm to 20 μm. "NUCLEPORE filters are commercially available from Corning Costar Corporation, 1 Alewife Center, Cambridge Mass. The microskin can then be formed upon the internal and external surfaces of this underlayment by one or more simple variants of the procedures described in Sections C and D below.

Alternatively, polycarbonate underlayments may also be fabricated by the above described membrane filter casting method.

4. Depth filters

So-called "depth filters" comprise a matrix of randomly oriented fibers, that are pressed, wound, sintered, or otherwise bonded together by methods known to and commonly practiced by one skilled in the art. Such depth filters have been fabricated from glass microfibers, and fibers of a variety of other polymers. Certain depth filters are commercially available from a number of suppliers (e.g., Millipore Corp., Bedford, Mass.; Amicon Corp., Bedford, Mass.; Gelman Sciences, Ann Arbor, Mich.). The microskin can then be formed upon the internal and external surfaces of the underlayment by one or more simple variants of the procedures described in Section C and D below.

5. Other microporous structures

The aforementioned examples are meant to illustrate but not to limit the scope of the methodology which can be employed now and in the future to create microporous underlayments.

B. ADDITIONAL MATERIALS COMPRISING UNDERLAYMENT COMPOSITION (singly or in combination)

In addition to the polymers cited in the sections above which describe the methods for fabrication of microporous membranes by filter casting and other means, instances will arise when additional polymers or polymer systems may constitute preferred embodiments of the current invention. For example, resorbable and biodegradable polymer systems are desirable embodiments of the invention in instances when removal of the implanted CND Controlled Release Device would require a medical procedure such as surgery, with the attendent risks thereof. Without wishing to be limited by the examples cited below, we cite some specific polymer systems suitable for fabrication into biodegradable/ bioresorbable polymer systems.

1. Polylactide/ Polyglycolide

Polylactide/polyglycolide copolymers have been used extensively in the form of biodegradable surgical sutures. They are polymers of choice for injection into humans in the form of microspheres for sustained drug delivery controlled by diffusion and bioerosion, and are available for that purpose from Stolle Research and Development Corp., Cincinnati, Ohio [Hutchinson, F. G. and Furr, B. J. A. (1990) J. Controlled Release 13, 279]. A salient reason for the desirability of this copolymer system for in vivo use is that the degradation products of this copolymer in vivo are lactic acid and glycolic acid, both of which are also products of human metabolism and as such are known to be non-toxic in the amounts generated by slow biodegradation of sutures or microspheres. Slow release microspheres and other devices have been used to deliver, among other agents, luteinizing hormone releasing hormone (LHRH) and its analogues. Said analogues. Among them Zoladax, in the form of a polylactide/polyglycolide subcutaneous implant [Dukman, G. A. et al. (1990) J. Steroid Biochem. Molec. Biol. 37, 993], are candidates for treatment of cancer of the prostate, endometriosis, and mammary cancer. LHRH analogues released in a sustained manner, among them Zoladax [Dukman et al, ibid] and Nafarelin [Sanders, L. M. et al. (1986) J. Pharm. Sci. 75, 356], are also candidates for use as female and male contraceptive agents. Based on the above considerations, said copolymer should be a system of choice for use as an underlayment for a CND Controlled Release Device.

A typical process for manufacturing microspheres of said copolymer [H. Maulding (1987) J. Contr. Release 6, 167] involves dissolving the copolymer in a solvent, methylene dichloride. A non-solvent "phase inducer", typically an aqueous phase, is added to generate microcapsules which form an emulsion containing microspheres with aqueous pores. If a water-soluble drug is added to said emulsion, it will be entrapped within the aqueous pores for subsequent slow release.

Based on knowledge in the field of one skilled in the art, a brief representation of which is illustrated above, one skilled in the art should be readily able to cast a membrane filter of said copolymer for use as an underlayment of a CND Controlled Release Device.

2. other polymers

Other monomers that are suitable for use as bioerodible polymers or components of copolymers thereof include the poly (ortho ester) ALZAMER and other poly (ortho esters). The hydrolysis rates of specific esters vary widely, and this property may be exploited to control the rate of bioerosion of polymers or copolymers made from said esters. The following ester linkages, listed in order of decreasing hydrolysis rates (based on in vitro data) are: ethylacetate, methylacetate, methyl-(2-chloroacetate), ethylpyruvate, methyl-(2,2-dichloroacetate), and dimethyl oxalate [J. Heller (1994) in notes from M.I.T. Summer Course, "Advances in Controlled Release Technology: Polymeric Delivery Systems for Drugs, Pesticides, and Foods"].

Polyanhydrides, among them fatty acid dimer polyanhydrides, have also been used for bioerodable drug delivery systems, as have dextrans and chemically cross-linked dextrans [J. Heller (1994) in notes from M.I.T. Summer Course, "Advances in Controlled Release Technology: Polymeric Delivery Systems for Drugs, Pesticides, and Foods"].

3. proteinaceous and polysacchride materials

Collagens, laminins, fibronectins, dextrans, glycosaminoglycans (GAGs), or any other material referred to above as suitable for use as a microskin (see below) may also be employed for fabrication of an underlayment by methods that include but are not limited to casting, spinning, compression of fibers or particles, spray-drying, and the like.

C. MICROSKIN COMPOSITION (materials used singly or in combination)

Among the many types of polymeric materials that may be considered in the construction of the device, naturally occurring extracellular matrix components are particularly attractive in that they are inherently biocompatible if chosen correctly, and possess intrinsic properties that may facilitate the proposed applications of the device. By far the most abundant classes of extracellular matrix proteins are the proteinaceous collagens and the polysaccharide glycosaminoglycans (GAGs). Less abundant, but of great significance are the matrix proteins of the fibronectin and laminin families.

1. Collagens

Collagens [Alberts, B. et al., eds. (1983) Molecular Biology of the Cell, New York, Garland, pp. 693–696] consist of a large class of related molecules that share common features. The individual collagen molecule is a fibrous, triple-stranded, helical structure composed of 3 separate polypeptide chains known as $\alpha$-chains, each approximately 1000 amino acids long. Different collagens vary in the stoichiometry of their $\alpha$-chains composition, and in their normal patterns of tissue distribution. Thus if maximal biocompatability is desired of a given device, it may be appropriate to make use of the collagen type that is normally present in the site of implantation. For example, Type I collagen predominates in tendons and ligaments, while Type II collagen predominates in cartilage. If it is desirable for the device to encourage cell attachment or infiltration, a collagen that promotes attachment or motility of the desired cell type should be used. For example, Type I collagen is reported to inhibit the proliferation of Schwann cells [P. A. Eccleston, R. Mirsky, and K. R. Jessen, Exp. Cell Res. 182: 173–185 (1989)] while Type IV collagen is normally produced by Schwann cells in contact with neurons [D. J. Carey, C. F. Eldridge, C. J. Cornbrooks, R. Timpl, and R. P. Bunge, J. Cell Biol. 97: 473–479 (1983)]. Thus Type IV collagen may be more appropriate for devices expected to promote normal Schwann cell behavior in peripheral nerve.

2. Glycosaminoglycans (GAGs)

GAGs are long unbranched polysaccharides consisting of repeating disaccharide units in which one sugar of the unit is an amino sugar [Alberts, B. et al., eds. (1983) Molecular Biology of the Cell, New York, Garland, pp. 702–704]. These molecules tend to be highly negatively charged due to their abundance of sulfate and carboxyl groups. Individual polymers vary greatly in molecular weight, but may range from 3,000–4,000 Daltons up to greater than 1,000,000 Daltons. Among the most well characterized are hyaluronic acid, chondroitin sulfate, dermatan sulfate, heparan sulfate, heparin, and keratin sulfate. As in the case of collagens, there are tissue-specific patterns of normal expression that may suggest particular GAG forms that will promote biocompatability. For example chondroitin sulfate is found primarily in cartilage, and dermatan sulfate is found primarily in skin. In relation to cell attachment and infiltration, the anti-adhesive qualities of chondroitin sulfate may inhibit cell attachment, while heparin or heparan sulfate may promote cell attachment and infiltration. The charged aspect of GAGs may also promote an association with therapeutic macromolecules that makes them particularly attractive in fabricating the skin component of the device. For example, members of the fibroblast growth factor (FGF) family of proteins are known to associate with heparin, and in the case of acidic FGF the presence of heparin can potentiate the factor's activity [D. Gospodarowicz and J. Cheng (1986) J. Cell. Physiol. 128, 475–484; J. Sudhalter, et al., (1989) J. Biol. Chem. 264, 6892–6897.]

3. Fibronectins and laminins

Fibronectins [R. Hynes, Ann. Rev. Cell Biol. 1, 67–90 (1985)] and laminins [G. R. Martin and R. Timpl, Ann. Rev. Cell Biol. 3, 57–85 (1987)] are minor components in most extracellular matrices but are potent substrates for cellular attachment. Fibronectins are covalent dimers with subunits each of approximately 250,000 Daltons. While classical laminin is a heterotrimer with 2 light chains of approximately 200,000 Daltons and 1 heavy chain of approximately 400,000 Daltons. Both have numerous attachment sites for other extracellular matrix proteins as well as cellular attachment sites. The most well known of the latter is amino acid sequence arginine-glycine-aspartate that is recognized by cell surface receptors known as integrins [R. O. Hynes, Cell 48, 549–554 (1987)]. These proteins may also be useful in the composition of the device for the reasons outlined above.

GAGs, fibronectins and laminins readily coat substrates when solubilized in physiological saline solution [Mahanthappa, N. et al. (1994) Development 128, 1373–1384]. A microskin can be formed by substituting said solution for the mildly acidic solution employed to create a collagen microskin over an underlayment (c.f. Examples 1 and 4).

4. synthetic polymers and chemical derivatization

Microskins may also be fabricated from a variety of synthetic polymers, including those listed below for fabrication of underlayments. Either synthetic polymers and/or biological polymers such as collagen and fibronectin may be derivatized to attach functional groups which may react under appropriate circumstances to form covalent bonds with the macromolecules one wishes to bind and release in a controlled manner. Formation of said covalent bonds may be desirable for attenuating the rate of release, stabilizing the bound macromolecule under circumstances when the cooperative noncovalent bonds are inadequate to immobilize said macromolecule(s) in a stable manner, or otherwise gaining increased control over the amount of macromolecule(s) bound and the time course of said macromolecule(s)' release.

D. Microskin fabrication methods

The microskin may be formed on the underlayment by the procedure described below and illustrated in FIGS. 1A, 1A-1 through 1A-5, and 1B. A specific detailed protocol for fabrication of a collagen microskin upon a microporous cellulosic underlayment is provided in Example 1, and a protocol for fabrication of a collagen microskin over a cellulosic underlayment is provided in Example 4.

While not wishing to be limited by the method described herein, a preferred method involves first finding a suitable means of dissolving the microskin material. In the case of collagen, dilute (0.1N) acetic acid can be employed. The microporous underlayment is then exposed to the microskin solution by allowing said solution to be drawn into the wettable micropores by capillary action. The external surfaces of the underlayment (see FIGS. 1A, 1A-1 through 1A-5, and 1B) are blotted free of excess microskin solution, and the resulting impregnated underlayment is allowed to slowly air dry. The temperature and humidity (or vapor pressure of the solvent if it is nonaqueous) may be adjusted to control the rate of drying. For the method described in Example 1, room temperature and ~50–70% relative humidity are appropriate if the material is allowed to air dry for 1–2 hours. The resulting structure is the underlayment with the internal porous network lined with a microscopic coating of microskin (c.f. FIGS. 1A, 1A-1 through 1A-5, and 1B).

The concentration of microskin material in the solvent solution may vary from ~0.01% to ~50% or higher by weight, but is preferably between 0.1% and 10% by weight. Example 1 illustrates the use of a 0.35%–0.4% collagen solution by weight as the coating of the cellulosic underlayment.

It is recognized that a variety of modifications of this method may be devised to achieve a satisfactory microskin coating on the underlayment in specific instances.

E. RELEASABLE MACROMOLECULES

The releasable macromolecule can be of a molecular weight exceeding about 400 daltons. The following are examples of such macromolecules.

1. Growth Factors

Of the many releasable macromolecules of therapeutic relevance that might be incorporated into the device described, polypeptide growth factors constitute a large category. Many of the known polypeptide growth factors fall into "families" of related structures. Ideally, controlled release by the Device described herein will allow focal administration of various polypeptide family members to appropriate target tissues by juxtaposition of the device within or near the target area.

a. Neurotrophins

Neurotrophins are the best characterized polypeptide growth factors in the nervous system [W. D. Snider, Cell (1994) 77, 627–638]. The current list of members includes nerve growth factor (NGF), brain-derived neutrophic factor (BDNF), and the neurotrophins NT-3 and NT-4. Each of these factors promotes the survival and differentiation of different but overlapping groups of neurons in both the peripheral and central nervous systems. In addition, both ciliary neurotrophic factor (CNTF) and leukemia inhibitory factor (LIF) [Y. Masu, E. Wolf, B. Holtman, M. Sendtner, G. Brem, and H. Thoenen, Nature (1993) 365, 27–32] play roles in the differentiation and maintenance of defined populations of neurons. Delivery of these molecules by the device described may rescue populations of neurons damaged by injury or disease, and promote neural regeneration.

b. Neuregulins and other members of the EGF family

Among the many members of the epidermal growth factor (EGF) family are EGF, transforming growth factor-α (TGF-α), amphiregulin, schwannoma-derived growth factor, heparin-binding EGF-like factor [T. F. Deuel, Ann. Rev. Cell Biol. (1987) 3, 443–492; J. Massague, and A. Pandiella, Ann. Rev. Biochem. (1993) 62, 515–541], and the neuregulins [M. A. Marchionni et al., Nature (1993) 362, 312–318]. Many of these molecules are known to be potent mitogens for various cells of epithelial origin. The neuregulins in particular are known to modulate the division and differentiation of mammary cells, to promote division of Schwann cells of the peripheral nervous system, and to induce expression of acetylcholine receptors at neuromuscular junctions. Delivery of these molecules by the device described may demonstrate utility in the treatment of diseased epithelia, and diseased or damaged regions of the nervous system.

c. Transforming growth factor family

The transforming growth factor-β (TGF-β) family of growth factors constitute a very large family of molecules with a variety of functions [J. Massague, Ann. Rev. Cell Biol. (1990) 6, 597–641]. The family includes TGF-β isoforms numbered 1–5, the activins, the inhibins, the bone morphogenetic proteins (BMPs) 1–7, and Mullerian inhibitory substance (MIS). The TGF-βs are primarily modulators of differentiation, inhibiting it in some cases (e.g. adipocytes and skeletal myoblasts) and promoting it in others (e.g. chondrocytes and a variety of epithelial cell types). Activins and inhibins modulate the production of follicle-stimulating hormone in pituitary cells, thus modulating fertility. The BMPs are key modulators of bone development and formation. MIS controls genital development during embryonic development. Delivery of these molecules by the device described may demonstrate utility in the control of proliferating cells of epithelial origin (e.g. mammary carcinoma cells), control of reproduction and fertility, and control of bone healing after injury or surgery.

d. Hematopoietic Growth Factors

A variety of structurally unrelated molecules are known to promote various aspects of blood cell formation [T. M. Dexter, and E. Spooncer, Ann. Rev. Cell Biol. (1987) 3, 423–441]. These include interleukins-3 and -4, a host of colony stimulating factors (G-CSF, M-CSF, and GM-CSF), and erythropoietin. The controlled release of these molecules by the device described implanted in various sites of hematopoietic activity may facilitate blood cell formation and reduce the doses necessary for attaining the therapeutic effects of these proteins as observed through systemic administration.

e. Other polypeptide growth factors

There are many more polypeptide growth factors that may be usefully delivered by the device described. Growth factors that are members of the fibroblast growth factor (FGF) family W. H. Burgess, and T. Maciag, Ann. Rev. Biochem. (1989) 58, 575–606] are potent mitogens for a variety of cells of ectodermal and mesodermal origin, and potent promoters of angiogenesis and vascularization. Similarly, insulin and the insulin-like growth factors (IGFs) are potent mitogens, and modulators of differentiation and metabolism [W. S. Cohick, and D. R. Clemmons, Ann. Rev. Physiol. (1993) 5.5, 131–153]. The activity of IGFs can in turn be modulated by polypeptides known as IGF-binding proteins [J. R. Florini, D. Z. Ewton, and F. J. McWade, Diabetes Reviews (in press)]. The platelet-derived growth factors (PDGFs) PDGF-AA, PDGF-BB, and PDGF-AB all possess a variety of tissue-specific mitogenic activities and can modulate the activity of other growth factors [T. F. Deuel, Ann. Rev. Cell Biol. (1987) 3, 443–492]. All of these polypeptide growth factors are macromolecules that could be administered by the device described.

2. Antibodies, esp. monoclonal antibodies, for a variety of therapeutic purposes.

The immune system of mammals shows great specificity in its response to a variety of antigens. This property has been exploited to generate antibodies that can be used for a variety of therapeutic goals, among them cancer therapy in which selective targeting of cell-specific antigens can be used to destroy cancer cells [Tomlinson, E. (1987) Advanced Drug Deliv. Rev. 1, 87–198; Shin, S. U. (1991) Biotherapy 3, 43–53]; antibodies which affect cell migration, e.g. antibodies which stimulate Schwann cell migration and in turn can may be useful to stimulate nerve regeneration [Matthews, W., unpublished results]; antibodies directed to vital or bacterial antigens which can be used to destroy infections by said antibodies or antigens.

While not wishing to be limited by the aforementioned examples, they serve to illustrate the therapeutic utility of the CND Controlled Release Device for controlled delivery of antibodies for therapeutic purposes. A preferred embodiment of this invention is its use for sustained release of monoclonal antibodies. By appropriate use of said Device, one can selectively target a therapeutic site, reduce the opportunity for degradation of the delivered antibody, and minimize toxicity of the delivered antibody.

3. Vaccines

Vaccines have been used for more than a century to stimulate the immune system to mount a defense to a disease-causing organism, among them viruses, bacteria, etc. With increasing awareness that multi-drug-resistant bacterial strains are evolving that are resistant to conventional antibiotic therapy, and the fact that certain virally-caused diseases (among them Acquired Immunodeficiency Syndrome [AIDS]) are yet to be overcome by the use of vaccines or conventional pharmacotherapy, there is great interest in the generation of more effective vaccines [Walker, B. D. (1994) J. Acquired Immunodef. Synd. 7 (Suppl. 1), S6–S13; Cease, K. B. and Berzofsky, J. A. (1994) Ann. Rev, Immunol. 12, 923–989].

One way in which a CND Controlled Release Device may be employed for that purpose is its use for controlled delivery of vaccines. Vaccines often take the form of heat-killed or otherwise altered viruses, bacteria, bacterial fragments, viral fragments, or components thereof. A property of the CND Controlled Release Device that makes it suitable for controlled delivery of vaccines when suitably implanted in a subject is the fact that, as stated above, a vaccine would be inaccessible to cell-mediated destruction when it is immobilized within the pores of an appropriate embodiment of said Device. Since the surfaces of viruses and bacteria contain proteins and other macromolecules which can afford their immobilization to the microskin of said device, one should readily be able to employ said Device for controlled delivery of vaccines. In addition to use of a CND Controlled Release Device for this purpose as an implant, said Device may also be employed as an extracorporeal device for vaccine administration and related indications.

4. Other chemical- and/or diffusion-controlled mechanisms for immobilization and release by a CND Controlled Release Device Up to this point, we have focused on cooperative noncovalent bonds as the sole mechanism governing immobilization and release of agents from the current invention. However, it is apparent that the use of other mechanisms for immobilization and release by this CND Controlled Release Device constitutes an improvement on the prior art. For example, when the pore size of the underlayment and/or the microskin approaches submicron dimensions and or the thickness of said Device approaches millimeter dimensions or greater, diffusion of the agent to be delivered out of said device may contribute to or even be the predominant process governing controlled release from said Device. Accordingly, we wish to emphasize that a suitably constructed CND Controlled Release Device may employ diffusion controlled controlled release as a process contributing primarily or secondarily to control of the kinetics of release from said device.

Likewise, covalent chemical bonds may be formed between the microskin and a releasable agent, and dissociation (e.g. hydrolysis and/or oxidation) of said covalent bonds may also be a process that plays a primary or secondary role in governing immobilization and release of an agent incorporated into a CND Controlled Release Device. For example, it is known that upon lyophilization or other means of dehydration of proteins, intermolecular disulfide bonds may form among proteins and or other sulfhydryl containing molecules. Accordingly, we wish to emphasize that a suitably constructed CND Controlled Release Device may employ controlled release controlled by covalent chemical bonds as a process contributing primarily or secondarily to control of the kinetics of release from said Device. Circumstances may arise in which it is desirable to chemically derivatize the microskin and/or the macromolecule to be bound to gain further control over the immobilization and/or kinetics of release from said device. Examples include the attachment of free sulfhydryl groups or free amino to the microskin for subsequent reaction with proteins by methods known to one skilled in the art.

5. Other macromolecules that may be bound and released by this invention

We recognize that, in addition to proteins and peptides, a variety of other natural and synthetic macromolecules will be capable of forming cooperative noncovalent bonds and/or reversible (e.g. hydrolizable or oxidizable) covalent bonds that make them suitable as agents that can be bound and released in a controlled manner by a CND Controlled Release Device. While not wishing to be limited by the following examples, natural or synthetic macromolecules include nucleic acids, polysaccharides, lipids, glycolipids, glycoproteins, and proteolipids.

F. DEVICES and GEOMETRIES of the MICROPOROUS COMPOSITE MEMBRANE

A CND Controlled Release Device, in the form of a thin, flexible, dimensionally stable composite membrane, may be readily formed into a variety of geometries tailored to specific applications. The following examples serve to illustrate a representative subset of such geometries, and should not be interpreted so as to limit the scope of the current invention:

1. A cylindrical annulus, suitable for use as the lining of guide tubes (c.f. Example 3 and FIGS. 3A through 3C, 4, and 5A through 5F).

2. A preformed permeable hollow fiber membrane cylinder, which in itself may be employed as a nerve guide tube (c.f. Example 4 and FIG. 2).

3. A coating of a permeable guide tube, with a secondary membrane designed to exclude macromolecules from without. For optimal nerve regeneration, it may be necessary or appropriate to create said tube in a manner that selectively allows the transport of some nutrients and macromolecules across said tube, while excluding larger macromolecules [V. Guenard, et al. (1992) J. Neurosci. 12, 3310–3320]. Hollow fibers with suitable semipermeable characteristics [P. Aebischer, V. Guenard, and S. Brace (1989) J. Neurosci. 9, 3590–3595] are readily fabricated by those of ordinary skill in the art, and are commercially available from, for example, Amicon Corp. of Bedford Mass., and Spectrapor Corp., with a variety of molecular weight exclusion limits ranging from ~1,000 to ~1,000,000 Daltons.

The permeability barrier of the Amicon product, for example, is on the inner surface of the hollow fiber, and said barrier may inhibit the transport of molecules from the walls of the nerve guide tube to the regenerating nerve within the tube. For this reason, it may be desirable to form the permeability barrier on the outer rather than the inner surface of said hollow fiber. This can be achieved by modification of the process initially employed for fabrication of said hollow fibers, said modifications being readily achievable by one of ordinary skill in the art.

Alternatively, other modifications of the process for fabricating a preformed hollow fiber CND Controlled Release Device may be considered. An ultrafiltration membrane, formed, for example, from a polyelectrolyte complex, may be added to the outer surface of the cylindrical annulus of the hollow fiber tube before or after the microskin is deposited on said tube. Such polyelectrolyte complexes may be formed, for example, in the following way (Michaels, A. S. et al., U.S. Pat. No. 3,558,744):

a. A solution of a positively charged polyelectrolyte such as polyvinyl benzyl trimethylammonium chloride (VBTAC) is absorbed into the pores of the hollow fiber membrane.

b. While the pores of the above treated hollow fiber membrane are still wet with the VBTAC solution, said hollow fiber membrane is dipped into a second solution of a suitable negatively charged polyelectrolyte such as sodium polystyrene sulfonate (NASS). The polyelectrolyte complex is formed as a thin skin at the outer surface of the hollow fiber membrane, and constitutes the desired semipermeable membrane. The resulting hollow fiber/polyelectrolyte complex membrane device is washed free of excess unreacted polyelectrolyte complex solution.

4. A ribbon or strip-like structure, suitable for implantation within a nerve guide tube (FIGS. 5C and 5D), subcutaneously, intravenously, or elsewhere in the body where local or systemic controlled delivery of proteins or peptides to a therapeutic target tissue is desired.

5. A threadlike structure, suitable for implantation within a nerve guide tube (FIGS. 5E and 5F), subcutaneously, intravenously, or elsewhere in the body where local or systemic controlled delivery of proteins or peptides to a therapeutic target tissue is desired.

6. A sheetlike structure suitable for implantation subcutaneously, intravenously, or elsewhere in the body where local or systemic controlled delivery of proteins or peptides to a therapeutic target tissue is desired.

It is appreciated that suitable modifications of the CND Controlled Release Device configurations described above may result in devices suitable for extracorporeal placement such as skin patches, intravenous infusion devices, and other extracorporeal devices for controlled delivery of proteins and/or peptides.

The CND Controlled Release Device can also be made as devices including buccal and oral devices, vaginal and intrauterine devices of cylindrical, bullet, elliptical, circular, bulbous, loop, bow or any other shape that is appropriate for placement into these biological environments. Said device also includes ocular devices of any geometric shape for comfortable placement in the cul-de-sac such as ellipsoid, bean, banana, circular, rectangular, doughnut, crescent, and half-ring shapes. In cross section an ocular Device can be doubly convex, concave-convex, etc. The dimensions of the ocular Devices can vary according to the shape of the eye, with said Device generally 4–20 mm in length, 1–15 mm in width, and 0.05 to 4 mm in thickness. Other devices within the scope and spirit of the invention include implants, anal suppositories or the like, pessaries, prosthetic devices, and artificial glands for dispensing a pharmaceutically desirable macromolecular agent having a physiological function akin to that of the natural gland. Also included are cervical, nasal, ear and skin devices.

G. Indications for therapeutic use of a CND Controlled Release Device:

We wish to preface this overview of representative indications for therapeutic use of controlled delivery by means of the current invention, by pointing out that new discoveries relating to the mechanisms and treatment diseases and disorders are constantly being made. We have developed the CND Controlled Release Device expressly for the purpose of treating a broad range of said disorders, based both on (a) currently known disease mechanisms and approaches to treatment by administration of peptides, proteins, other macromolecules, and other agents such as vaccines; and on (b) disease mechanisms and approaches to treatment by administration of the aforementioned agents that are yet to be discovered. Below we provide a perspective on said mechanisms and treatment strategies that are currently established, as well as a relevant subset of those that may evolve from basic research that is now in progress.

1. Use in nerve guide tubes and other nerve regeneration paradigms

As described in detail below ("Preferred Embodiment") and in Examples 2 through 6, nerve regeneration may be aided by exposure to any of a number of trophic factors or related agents such as migration- and/or proliferation-inducing antibodies. As such, this constitutes a preferred embodiment of this invention.

2. Use to treat disorders of pituitary function (e.g, thyroid or growth deficiency)

Certain hypersecretory disorders may result from abnormal activity of cells within the central nervous system, among them cells of the pituitary gland, also termed the hypophysis, located at the base of the brain. Secretion of hormones and related substances from cells of the adenohypophysis is regulated by releasing factors, primarily those secreted by the hypothalamus [Cooper, P. E. and Martin, J. B. (1992) in Diseases of the Nervous System: Clinical Neurobiology, Asbury et al. eds. Saunders. Philadelphia. pp. 567–583]. Substances secreted by the adenohypophysis include growth hormone, prolactin, thyroid stimulating hormone (TSH), and adrenocorticotrophic hormone (ACTH). Hypersecretion of these substances from the pituitary can lead to a variety of disorders of growth (e.g. acromegaly due to hypersecretion of growth hormone) and metabolism (e.g. secondary hyperthyroidism triggered by hypersecretion of TSH, and Cushing's disease, which results from excessive secretion by the pituitary of precursor peptides containing ACTH) [see Cooper, P. E., and Martin, J. B. ibid.]. These disorders are often due to benign tumors of the pituitary secretory cells. Conversely, hyposecretion of said peptide hormones may also lead to diseases or disorders, among them dwarfism (due to hyposecretion of growth hormone) and hypothyroidism (due to hyposecretion of thyroid hormone).

Appropriate pharmacotherapy that entails controlled release of pituitary peptides, pituitary releasing factors, or peptide antagonists thereof, could be achieved by use of the current invention. While not intending to be limited by this example, for the purpose of direct influence of pituitary function, brain implants of a biocompatible version of the CND Controlled Release Device may be desirable. An additional desirable property of such an implant may be biodegradability. Brain implants of devices of the prior art are currently under active investigation.

Secretion from the neurohypophysis of the pituitary is regulated by innervation from elsewhere in the CNS. For example, the release of oxytocin and vasopressin is regulated at least in part by the activity of neurons in the paraventricular nucleus of the hypothalamus, which innervates the neurohypophysis. Controlled delivery of compounds known at present or shown in the future to be useful in treatment of disorders of secretion of substances from the neurohypophysis, among them dilutional hyponatremia, which is believed to be caused by inappropriate secretion of vasopressin [see Martin, J. B., and Reichlin, S., Clinical Neuroendocrinology, 2nd Edition (1987) Philadelphia, Davis].

By the aforementioned rationale, controlled release of appropriate peptides and/or proteins using the current invention may also be useful for treatment of disorders involving hypersecretion of substances produced by the hypothalamus, among them diabetes insipidus, which may be caused by hypersensitivity to, or excessive release of, vasopressin ("AVP"). AVP is a peptide synthesized in and released from neurons of the supraoptic and paraventricular nuclei of the hypothalamus [see Cooper, P. E., and Martin, J. B. in Diseases of the Nervous System: Clinical Neurobiology, Asbury et al., eds, Saunders, Philadelphia (1992), pp. 567–583]. A current means of treatment of diabetes insipidus is surgical destruction of most of the cells in the supraoptic nucleus. Pharmacotherapy involving controlled release of a peptide or protein antagonist of AVP by means of the current invention may in some instances obviate the need for such neurosurgery.

In some instances pharmacotherapy employing controlled release of peptide antagonists of pituitary releasing hormones may obviate the necessity and attendent risk of neurosurgery performed for the purpose of removing benign tumors of the pituitary which cause hypersecretion.

3. Controlled delivery of GGF's and other members of the neuregulin family

The pituitary has been hypothesized to secrete growth factors. Among them are members of the aforementioned neuregulin family of proteins, termed glial growth factors ("GGF's"), that are mitogenic for myelin-forming Schwann cells, and as such may play an important role in development and regeneration of the nervous system [Marchionni et al. (1993), Nature 362, 312–318]. GGF's are structurally related to neuregulin family members which are known to activate c-neu and related members of the EGF receptor family of tyrosine kinases, including the heregulins [Holmes, W. E. et al. (1992), Science 256, 1205–1210], and neu differentiation factor [Wen, D. et al. (1992), Cell 69, 559–572].

Bovine pituitary glands have been identified as an enriched source of GGF's, and a GGF of $M_r$ 31,000 has been purified from bovine pituitary [Lemke, G. E. and Brockes, J. P. (1984), J. Neurosci. 4, 75–83]. Multiple molecular forms of GGF may be secreted from the pituitary, either in active form or as precursors. GGF's from bovine pituitary extracts can be resolved into at least 3 activities with different molecular masses: GGF-1 (34,000), GGF2 (59,000), and GGF3 (45,000) [Goodearl et al. (1993), J. Biol Chem. 268 18095–18102].

The gene for human GGF2 has been cloned and expressed in cell lines which secrete recombinant GGF2. Said recombinant GGF2 and a homologous protein, termed "ARIA", have been shown to exert a robust trophic effect on myoblast cells, which are muscle cell precursors [Robert Sklar, Cambridge NeuroScience, unpublished data and Falls, D. L. et al. (1993) Cell 72, 801–815]. These results suggest that GGF's and related proteins may also be involved in the development, maintenance, and/or regeneration of muscle.

The precise role of GGF's and the aforementioned related proteins in the development, maintenance, and/or repair of the nervous system and muscle has yet to be elucidated, and the manner and loci of secretion of GGF's and related molecules has yet to be defined. However it is reasonable, based on existing evidence, to hypothesize that pathophysiological circumstances may arise in which it may be desirable to regulate the secretion of GGF's and related proteins from the pituitary and/or other secretory sites. One possible circumstance may be diseases that involve the deterioration of nerve, for example diabetic neuropathy [Duchen, L. W. (1983) in Autonomic Failure: A Textbook of Clinical Disorders of the Nervous System, Bannister, R., ed., N.Y., Oxford Univ. Press; Foster, D. W. (1987) in Harrison's Principles of Internal Medicine, 11th Ed., New York, McGraw-Hill, pp. 1788–1795], or the deterioration of muscle, among them muscular dystrophies [Brooke, M. H. (1985) A Clinician's View of Neuromuscular Disease, 2nd ed., Baltimore, Williams and Wilkins; Huges, S. M., and Blau, H. M. (1990) Nature 345, 350–352].

Accordingly, pharmacotherapy involving controlled delivery by the current invention of GGF'(s), other members of the neuregulin family, or other trophic factors, among them insulin-like growth factors (IGF's) and fibroblast growth factors (FGF's) may correct disorders treatable by GGF/neuregulin replacement or supplementation, among them those listed above.

4. Use to prevent tumor growth and as a contraceptive depot (e.g., treatment of breast cancer, prostate cancer)

Based on the aforementioned success in vivo of controlled release of LHRH analogues in in vivo trials of treatment of mammary and prostate cancer, and there demonstrated potential as contraceptive agents, a CND Controlled Release Device may prove suitable as a depot for controlled delivery of said LHRH analogues, and other peptides and proteins for therapy of cancer and for contraception.

5. Delivery of TGFβ and related molecules for limitation of ischemic brain damage.

Transforming growth factor β1 (TGFβ1) has been shown to reduce infarct size after experimental cerebral ischemia in a rabbit model [Gross, C. E. et al. (1993) Stroke 24, 558]. TGFβ1 and IGF-1 also display therapeutically relevant effects in rat models of hypoxic/ischemic brain injury (Williams et al. [1994], in Proceedings of the 2nd Int'l. Neuroprotection Conf., Lake George, N.Y., Ann. N.Y. Acad. Sci., in press]. Based on these results, controlled delivery of members of the TGF and/or IGF family may be a viable neuroprotective therapy. Additional research in progress has set the stage for a variety of other proteins and peptides as neuroprotective agents, among them the cone snail peptide SNX111 (ω-conctoxin M-VII-A) [Valentino, K. et al. (1993) Proc. Nat. Acad. Sci. USA 90, 7894]. Because said peptide has toxic side effects, among them severe hypotension, controlled and/or local delivery of said peptide using a CND Controlled Release Device may improve its efficacy/safety ratio.

6. Additional general considerations for applicability of the CND Controlled Release Device In general terms, the CND Controlled Release Device can be manufactured into therapeutic systems and shapes akin to those described above for delivering a physiologically and/or pharmacologically active macromolecule that produces one or more localized or systemic effects in animals, including warm blooded animals, humans and primates, sport and farm animals such as sheep, goats, cattle, horses and pigs, for administration to laboratory animals such as rodents, and to avians, fish, reptiles and zoo animals. The amount of macromolecular agent released for a CND Controlled Release Device is, in its preferred embodiment, in excess of the amount needed to satisfy the required dosage regiment over a prolonged period of time, for example up to 6 hours, one day, days, weeks, months, or years.

H. Other uses of a CND Controlled Release Device

A suitable embodiment of a CND Controlled Release Device may be employed for controlled delivery of a variety of macromolecular substances for uses beyond therapeutics. While not wishing to be limited by the following examples, they serve to illustrate the range of application of said Device. This Device may be used for controlled release of enzymes to clean septic tanks, sink drains, and other plumbing appurtenances; for release of anti-algal agents or other suitable substances to control toxic algal blooms, among them the so-called "red tide", which releases the neurotoxin saxitoxin; for controlled release of insecticides for prevention of crop damage and for household use; for controlled release of insect pheromones; and to release macromolecular substance such as plant growth hormones and the like to encourage plant growth.

I. A PREFERRED EMBODIMENT: CONTROLLED RELEASE of rhGGF2 and/or FGF from a MICROPOROUS COLLAGEN/COMPOSITE MEMBRANE.

To illustrate the properties, advantages, and working principles of this invention, we further provide a detailed illustration of a preferred embodiment of the invention: its use to aid nerve regeneration. This specific example describes the fabrication and uses of a microporous CND controlled release membrane (termed "CND Controlled Release Device"). This example is intended to illustrate, but not to limit the scope or broad utility of the CND Controlled Release Device.

To optimize the therapeutic potential of growth factors as facilitators of nerve regeneration, it is desirable to control their delivery to the site of nerve repair. Recombinant human glial growth factor 2 ("rhGGF2"), a product of the neuregulin gene, stimulates rat Schwann cell proliferation and DNA synthesis in cell culture [Marchionni et al. (1993) Nature 362, 312–318]. The half-life of biological activity is less than 24 hours when soluble rhGGF2 is added to a polyethylene nerve guide tube reconnecting the two cut ends of rat sciatic nerve (Example 7 and FIG. 6). Nerve regeneration, and the Schwann cell proliferation that accompany functional restoration of a cut nerve, normally takes at least several weeks [Bunge, R. P. and Griffin, J. W. (1992) in Diseases of the Nervous System: Clinical Neurobiology, Asbury, A. K. et al. eds, Philadelphia, W. B. Saunders; R. D. Madison, S. J. Archibald, and C. Kraup (1992) in Wound Healing: Biochemical and Clinical Aspects, edited by I. K. Cohen, F. Diegelman, and W. J. Lindblad; W. B. Saunders Co., Philadelphia, Pa.; p. 450–487]. Nerve cut injuries, inflicted for example by knife or projectile wounds, are a significant cause of disability. An accepted method of therapy in many such cases is to resect the nerve within a guide tube, leaving a gap of several millimeters or more between the two ends of the cut nerve due to loss of an irretrievably damaged section of injured nerve (FIG. 5A through 5F).

To create a CND Controlled Release Device that can be used within the nerve guide tube to aid nerve regeneration, a form of this invention was created that would be compatible for placement as a lining, strip, or threadlike structure within the nerve guide tube (c.f. FIG. 5A through 5F). Based on the evidence indicating that rhGGF2 and/or fibroblast growth factors ("FGF") may enhance nerve regeneration [Aebischer, P. et al. (1989) J. Neurosci. Res. 23, 282; P. G.

Cordeiro, et al., (1989) Plastic Surg. Reconstr. Surg. 83, 1013–1020; and the above referenced Madison papers], the initial goal of this study was to determine whether said trophic factors can be bound and released in quantities sufficient to prolong Schwann cell proliferation within a nerve guide tube. This technology can be employed in a rat model of sciatic nerve repair to demonstrate therapeutic utility in a manner that can be adapted for human therapeutic use.

A composite microporous structure comprising an underlayment of mixed esters of cellulose and a microskin of collagen has been developed for this purpose, and was fabricated in the manner described in Example 1. RhGGF2 was exposed to this microporous membrane (thickness ~150 μm) under mildly acidic conditions; secondary bonds within the collagen matrix were broken, and reformed when the pH was raised in a manner that incorporates rhGGF2 within the membrane (Example 2).

Figure 4:
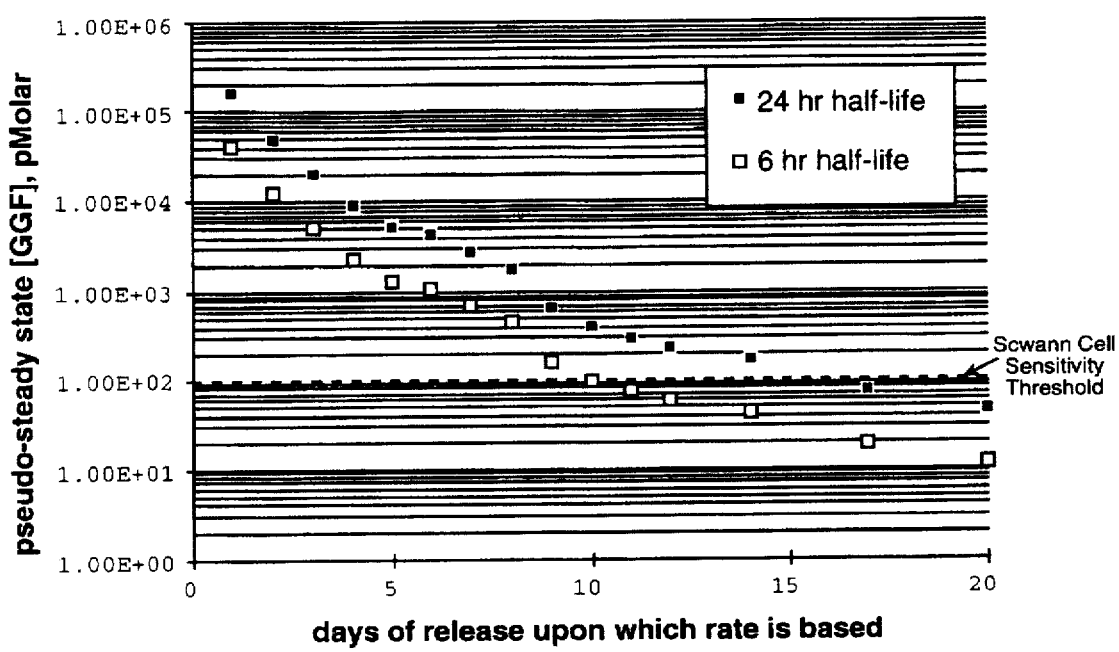
Figure 7:
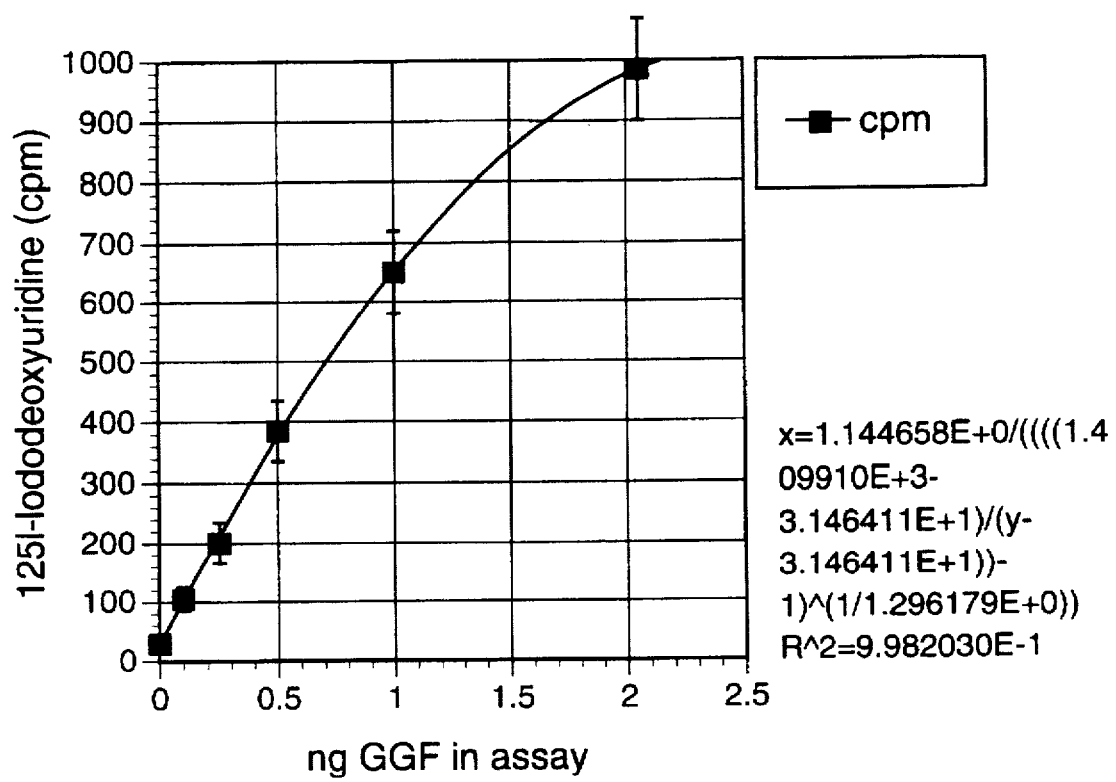
FIG. 7 illustrates the concentration dependent ability of rhGGF2 to stimulate Schwann cell mitogenesis as measured by the enhancement of radiolabled iododeoxyuridine ($[^{125}I]$ UDR) incorporation into Schwann cell cultures in vitro.
Figure 8:
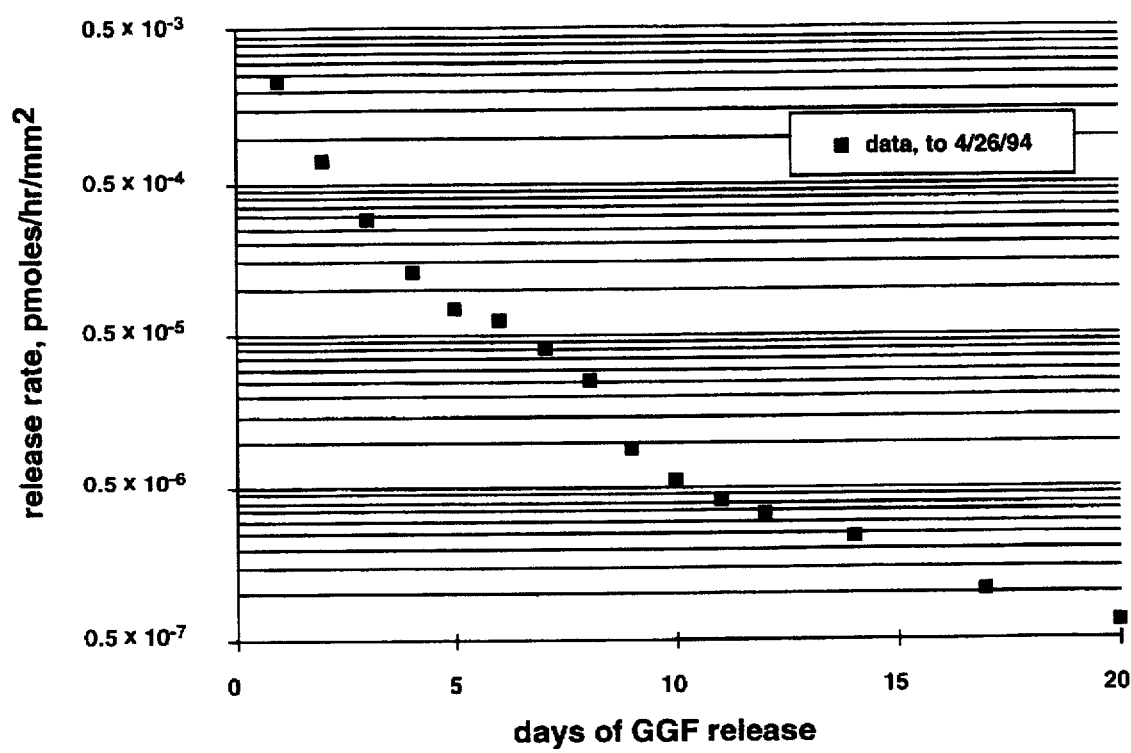
FIG. 8 illustrates the release of rhGGF2 bound within a CND Controlled Release Device formed from a collagen microskin over a cellulosic underlayment, expressed as amount released per $mm^2$.
Figure 9:
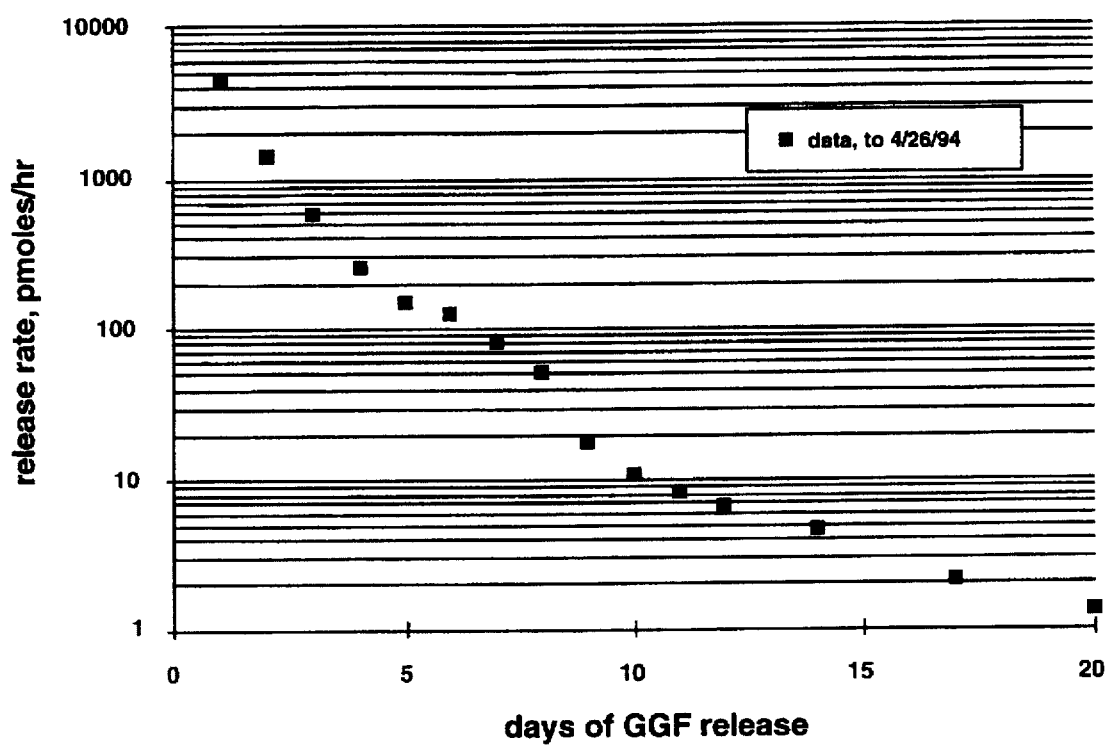
FIG. 9 displays the rate of release of rhGGF2 from a CND Controlled Release Device in vitro in terms of the rate of change of [rhGGF2] (pmolar per hour) where said device was employed to line a nerve guide tube in vivo.

Schwann cell $[^{125}I]$-uridine (or $[^3H]$-thymidine) incorporation was employed in vitro as a marker for release of rhGGF2 (FIG. 7). The rate of release was determined to exceed $0.5 \times 10^{-6}$ pmole/hr per $mm^2$ of membrane surface over a period of at least two weeks. Following an initial burst of release during the first day, the release rate declines in a manner approximating first order kinetics (FIG. 8). A mathematical model of a 1.4 mm diameter nerve guide tube lined with this membrane predicts that at the aforementioned release rate, [rhGGF2] would increase at a rate of >10 pMolar per hour throughout this two week period (FIG. 9). Based on preliminary estimates of the half-life of soluble rhGGF2 within a nerve guide tube in vivo in rats, and an EC50 of ~100 pM for stimulation of Schwann cell proliferation [c.f. $[^{125}I]$-uridine incorporation in vitro (FIG. 7)], the model predicts that by this means of controlled release, [rhGGF2] will exceed that required for stimulation of Schwann cell mitogenesis for said two week period (FIG. 4). In contrast, our data predict that rhGGF2 injected into a nerve guide tube would exhibit a much more rapid decline in concentration, and is much more sensitive to the half-life of degradation (FIG. 10).

Basic fibroblast growth factor (bFGF), which has also been shown to exert a therapeutic relevant effect on nerve regeneration [Aebischer, P. et al. (1989) J. Neurosci. Res. 23, 282]) can be bound and slowly released from the CND Controlled Release Device with similar kinetics (Example 5 and FIG. 11 ), affording the opportunity to employ the CND Controlled Release Device for controlled release of bFGF to aid nerve repair. FGF's may be used singly or in combination with rhGGF2 or other members of the neuregulin family to enhance the process of nerve regeneration. Using variants of the same method disclosed in this preferred embodiment of the invention, one of ordinary skill in the art should be able to release other trophic factors including neurotrophins, antibodies, and other therapeutically relevant proteins and peptides.

EXAMPLES OF THE INVENTION

The following examples are designed to illustrate certain aspects of the present invention. The examples are not intended to be comprehensive of all features and all embodiments of the present invention, and should not be construed as limiting the claims presented herein.

Example 1

Preparation of a cellulosic underlayment device with a collagen outer skin (See also FIGS. 1A, 1A-1 through 1A-5, and 1B)

(ALL PROCEDURES ARE PERFORMED UNDER STERILE CONDITIONS)

PREPARATION of Millipore cellulose acetate/cellulose nitrate filter and collagen solution:

a. autoclave Millipore SSWP-025-00, type SS, 3.0 micron filters.
b. autoclave filter paper the size that fits into the tops of the 60×15 mm Petri dishes
c. autoclave gauze for tamping the coated filters
d. prepare collagen, type I (Collaborative, #40236) by adding enough glacial acetic acid such that the final concentration of the acid was 0.1N HOAc (the original concentration of the HOAc from Collaborative was 0.02N)—the final collagen concentration was 3.5–4.0 mg/ml depending on the batch from Collaborative 2. Coating collagen microskin on underlayment of cellulose nitrate/acetate:

Day 1 a. pour the prepared collagen into a Petri dish and carefully "float" the autoclaved Millipore filters on top of the collagen—as the filters wet, gently help them submerge in the collagen—allow the filters to incubate overnight at room temp.

Day 2 a. pick the filters out of the collagen and tamp off the excess collagen on the autoclaved gauze—allow the filters to stand vertically against the side of the Petri dish to dry
b. after the filters are dry (~1–2 hours), they can be punched out into small discs using a 7/32 punch of diameter of 6 mm

Example 2

Fabrication of a CND Controlled Release Device_for slow release of recombinant human glial growth factor (rhGGF2)

a. A controlled release membrane (CRM) was fabricated with a collagen outer skin and cellulosic underlayment, by the methods described in Example 1.
b. On "day 2", as referenced in Example 1, the rhGGF2, at a [protein] of 162–225 μg/ml, is then added to the discs (5 μl of a known concentration of growth factor, or 5 μl of the vehicle control per disc), and the discs are appropriately arranged and an extra pool of factor is added so that the filters do not dry out. The vehicle is phosphate buffered saline ("PBS", as defined below).
c. the top of the Petri dish in which the discs are placed is lined with an autoclaved filter that has been soaked with sterile water again to help prevent drying out of the filters
d. the small Petri dish is then placed in a larger Petri dish in which water has been placed and then the large Petri dish is sealed with PARAFILM and allowed to incubate overnight at room temp.

Day 3 a. the filters are separated and allowed to air dry at room temp for approximately 1 hour

Example 3

Slow release of rhGGF2 in vitro (See also FIG. 8 (release per area) and FIG. 9 (total release)

a. the filters containing immobilized GGF, prepared as defined in Example 2, are then placed in a 96 well tissue culture plate and 5% HIFCS (50 to 100 μl Heat inactivated fetal calf serum/Dulbecco's modified Eagle's medium/1 g glucose per liter) is added to each well.

b. The protocol for collection of medium containing released GGF is initiated. At each time point medium is withdrawn, the filters are washed with 50–100 μl PBS, and the media is added for the next time point. All the time point samples are then frozen for assay.

The vehicle control that was used in these experiments involved subjecting the discs of Example 1 to treatment with PBS in the absence of rhGGF2. The composition of PBS is 0.05M NaPO4, 0.15M NaCl, pH 7.4. No significant release as measured by the rat Schwann cell DNA synthesis assay was ever observed.

Protocol for the rat Schwann cell DNA synthesis assay

Rat neonatal sciatic nerve Schwann cells were prepared, and the Schwann cell DNA synthesis was performed, using the methods of Brockes et al. [(1987) Meth. in Enzymol. 147: 217–225], incorporated by reference. (See FIG. 7 for standard curve)

Example 4

Figure 2:
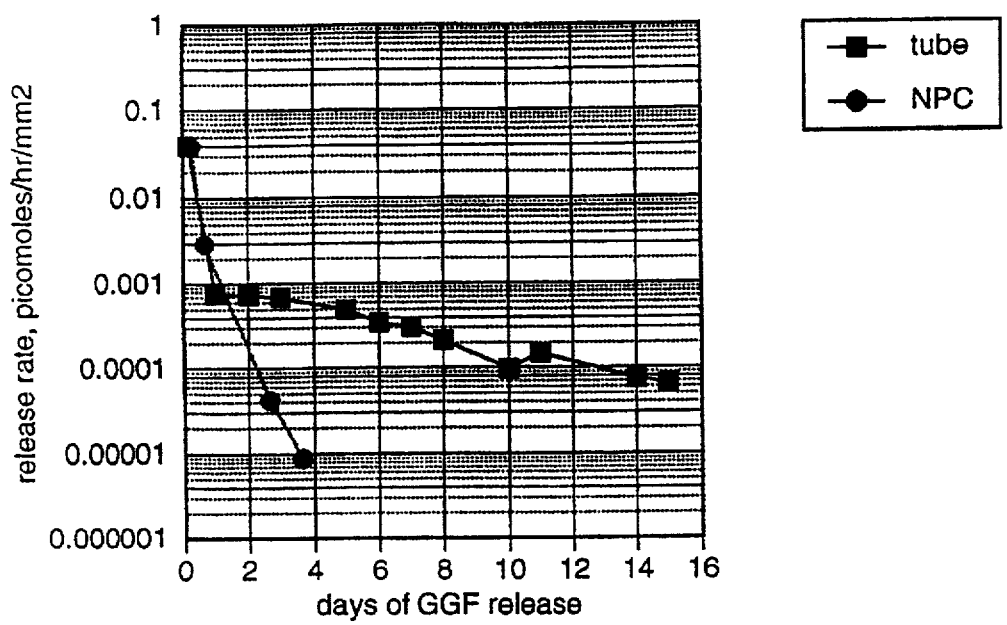
Figure 3A:
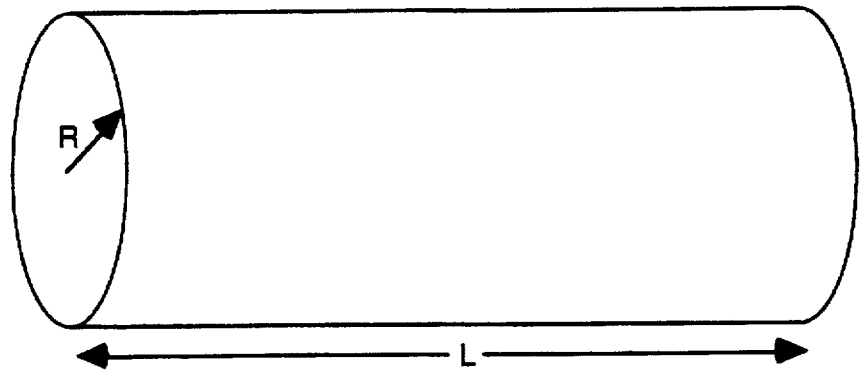
Figure 3B:
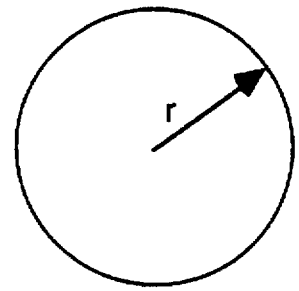

Hollow Fiber Release Study Protocol (See also FIG. 2)

Polysulfone Hollow fibers of molecular weight 30,000 were obtained form an Amicon H1P 30–43 Dialysis Cartridge. The outer casing was sawed at both ends and the fibers were cut off from the potting at one end. The fibers were soaked under running ultrafiltered water for approximately 2 hours to remove any glycerin coating. The fibers were stored at 4° C. in sterile ultrafiltered water or sterile phosphate buffered saline (PBS).

Segments of hollow fiber tubing were filled with an excess of type I rat tail collagen (3.5–4.0 mg/ml) (Collaborative Biomedical Products) which had its acetic acid concentration raised to 0.1N. The tubes were incubated overnight at room temperature in a humid environment, in said collagen solution. The tubes were cut into 5 mm lengths and allowed to air dry in the culture hood for a couple of hours. Five microliters of the 225 μg/ml GGF solution was injected from a pipette tip into the lumen of each 5 mm fiber length. The crest of the GGF solution droplet could be seen broaching the exiting orifice. These segments were then allowed to incubate overnight at room temperature in a humid environment.

Each segment was placed in a well of a 96 well plate. 100 μl of 10% heat inactivated fetal calf serum containing media (DMEM/low glucose) was added to the wells holding the tubes. At each time point, the 100 μl of solution was removed and stored frozen at −34° C. for assaying at a later time. The samples were rinsed with 100 μl of sterile PBS and then 100 μl of 10% serum containing media was replaced.
Bioassay
Protocol for the rat Schwann cell DNA synthesis assay Rat neonatal sciatic nerve Schwann cells were prepared, and the Schwann cell DNA synthesis was performed, using the methods of Brockes et al. [(1987) Meth. in Enzymol. 147: 217–225], incorporated by reference, with one significant modification:. $H^3$ thymidine incorporation rather than incorporation of $^{125}$I-iododeoxyridine was measured.
Nonporous Collagen Film Release Study Protocol Collagen films were fabricated by placing a pool (1 ml) of type I rat tail collagen solution on a sheet of PARAFILM and allowing it to dry overnight. The collagen solution had its acetic acid concentration raised to 0.1 Normal. The resulting collagen film was peeled from the PARAFILM and cut into circles (that would fit into the wells of a 96 well plate.). An excess of 5 μl of the 162 μg/ml GGF solution was placed upon each collagen circle. These were then allowed to incubate overnight at room temperature in a humid environment.

Each circle was placed in a well of a 96 well plate. 100 μl of 5% serum containing media was added to the wells holding the collagen films. At each time point, the 100 μl solution was removed and stored at −37° C. for assaying at a later time. The samples were rinsed with 100 μl of sterile PBS and then the 100 μl of 5% serum containing media was replaced.
Bioassay 96 well plates were prepared for the Schwann Cell challenge assay, performed as above. Ten microliters from each sample was placed into each of four wells. The $H^3$ Thymidine bioassay was performed as stated above and as shown in FIG. 7.

Example 5

Figure 11:
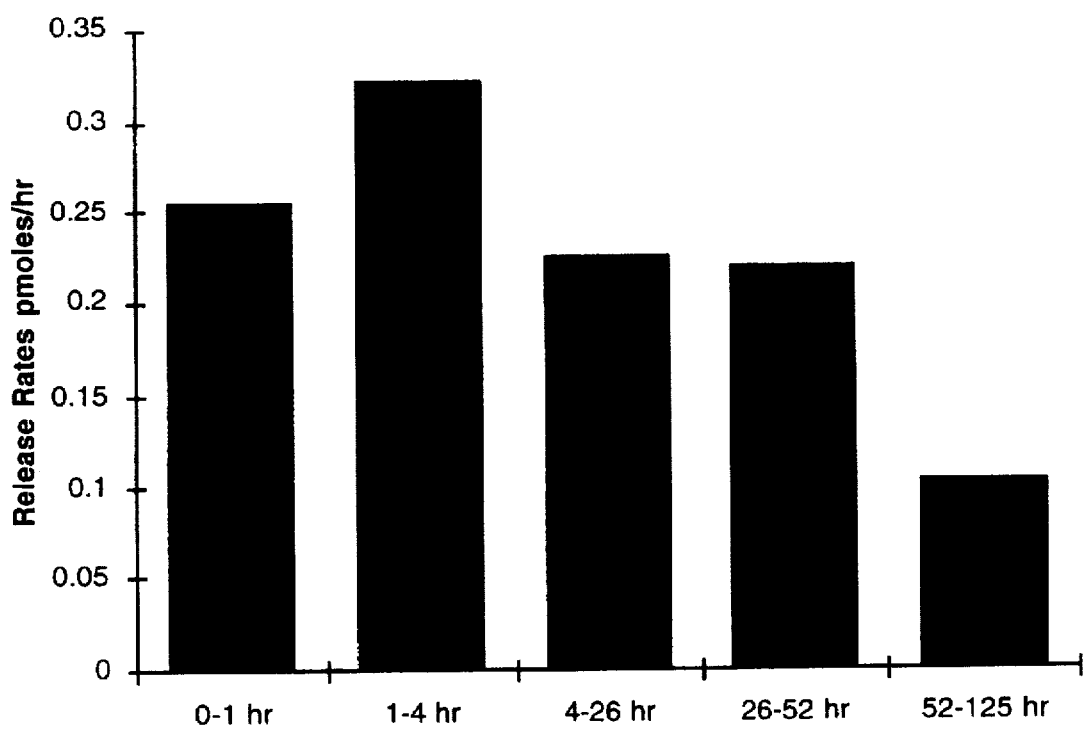
FIG. 11 illustrates controlled release of basic fibroblast growth factor ("bFGF") from a CND Controlled Release Device in vitro.

Fabrication of a CND Controlled Release Device for slow release of basic fibroblast growth factor (bFGF) (See also FIG. 11)

a. A controlled release membrane (CRM) was fabricated with a collagen outer skin and cellulosic underlayment, by the methods described in Example 1.

b. On "day 2", as referenced in Example 1, the bFGF, at a [protein] of 66.7 μl, is then added to the discs (5 ul of a known concentration of growth factor, or 5 ul of the vehicle control per disc), and the discs are appropriately arranged and an extra pool of factor is added so that the filters do not dry out.

c. the top of the Petri dish in which the discs are placed is lined with an autoclaved filter that has been soaked with sterile water again to help prevent drying out of the filters d. the small Petri dish is then placed in a larger Petri dish in which water has been placed and then the large Petri dish is sealed with PARAFILM and allowed to incubate overnight at room temp.

Day 3 a. the filters are separated and allowed to air dry at room temp for approximately 1 hour b. the filters are then placed in a 96 well tissue culture plate and Dulbecco's low glucose modified Eagle's Medium (1 g/liter of glucose) is added c. The protocol for collection of medium containing released GGF is initiated. At each time point medium is withdrawn, the filters are washed with PBS, and the media is added for the next time point. All the time point samples are then frozen for assay. The vehicle control that we used in experiments monitor slow release was to subject the discs of Example 1 to treatment with Dulbecco's Phosphate Buffered Saline (Ca and Mg free) in the absence of basic FGF (bFGF). No detectable stimulation of Schwann Cell DNA synthesis was observed in any of these control experiments.

Example 6

Slow release of basic fibroblast growth factor (bFGF) in vitro

Slow release of bFGF was determined in essentially the same manner as the method of Example 3 for measuring slow release of rhGGF2.

Example 7

Figure 6:
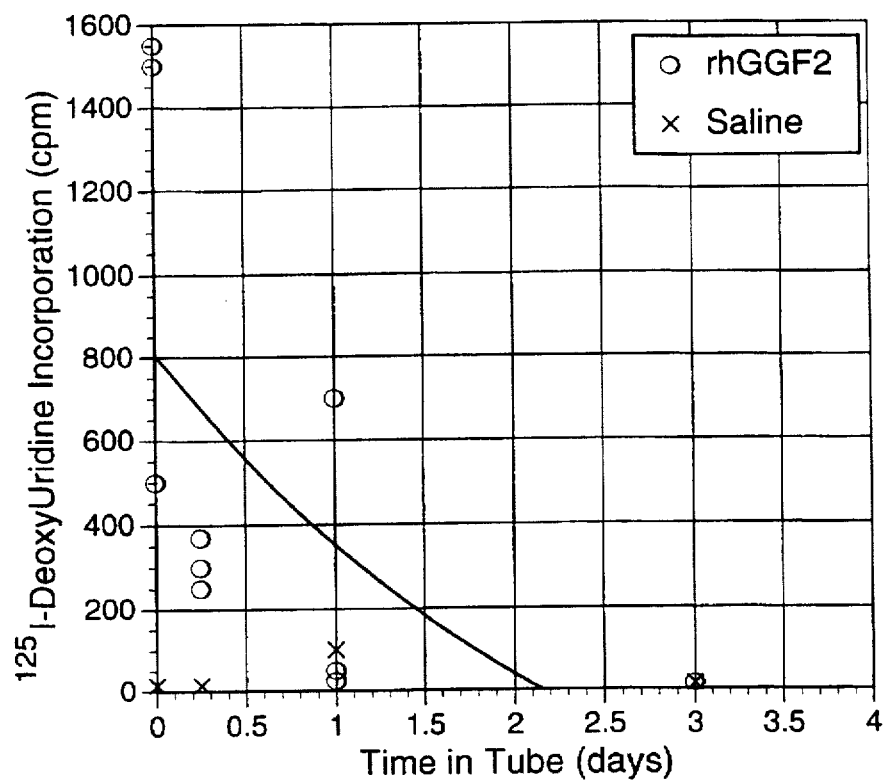
FIG. 6 illustrates the rapid decay of rhGGF2 when it is injected into the lumen of a nerve guide tube bridging a cut rat sciatic nerve; a view of each configuration is presented along with an enlarged cross-sectional view of the alternate device configurations within the nerve guide tube in vivo.

Measurement of the in vivo half-life of rhGGF2 in a nerve guide tube (see also FIG. 6).

A. Protocol

1) Thaw and combine two vials of 100 μl rhGGF2 (49.5 ng/μl; sample labeled: "GGF1st 71993 4.95 μg/100 ml HIC 9-9-93"). Add 2×122.75 μl sterile saline (245.5 μl) and 2 ×24.75 μl of 10 mg/ml Rat Serum Albumin (RSA) (49.5 μl) to make 495 μl solution of 20 ng/μl rhGGF2 with 1 mg/ml RSA in sterile saline. Aliquot 20 μl/tube into 23 microcentrifuge tubes and freeze at −30° C.

2) Add 50 μl of 10 mg/ml RSA to 450 μl sterile saline to make 500 μl solution of 1 mg/ml RSA in sterile saline. Aliquot 20 μl/tube into 23 microcentrifuge tubes and freeze at −30° C.

3) Reattach distal and proximal stumps of adult rat sciatic nerve (mid-thigh) with a polyethylene (PE) tube: remove 7 mm of nerve; use 13 mm length of PE tube; proximal-distal stump gap=10 mm.

4) Defrost and add rhGGF2 (or saline) to PE tube in vivo (20 ng/μl) and recover solution at time point t (t=0, 6 hour, 1, 3, 5 days) using a sterile 25 μl Hamilton syringe.

5) Place recovered solution (4–11 μl) in sterile microcentrifuge tube (500 μl). Estimate volume of recovered solution (×μl).

6) Pulse spin 30 sec in microcentrifuge and remove 4 μl of solution (max. dose=20 ng/μl=80 ng) into 36 μl media with 5% FCS and freeze immediately in 70% ethanol cooled on dry ice (1:10 dilution; max. dose=80 ng/40 μl=2 ng/μl rhGGF2 in media with 5% FCS).

7) After collecting all necessary time points, t, thaw samples and use 3 aliquots of 10 μl each (max. 20 ng/well) to test in triplicate the mitogenic activity with the in vitro Schwann cell proliferation assay (incorporation of $^{125}$I-iododeoxyridine).

8) Plot Schwann cell proliferation activity (cpm) vs. time in tube to measure in vivo half-life of rhGGF2.

| Experimental Animals For In Vivo Half-Life Study | | | | |
|---|---|---|---|---|
| Sample/Time | 0 Hour | 6 Hour | 1 Day | 3 Day |
| rhGGF2 | 3 | 3 | 3 | 3 |
| Control | 3 | 3 | 3 | 3 |

Number of experimental animals = 24

B. Results

FIG. 6 illustrates the fact that there is no detectable rhGGF2 activity in the control animals during the 3 day period of the experiment, as measured by stimulation of [$^{125}$I]-iododeoxyuridine incorporation. It further illustrates that the average rhGGF2 activity level has dropped to less than half by six hours in these rats, and in two out of three animals activity was lost completely by 24 hours. At 3 days, no activity could be recovered in any of the animals receiving rhGGF2. This rapid loss of rhGGF2 activity within the nerve guide tube has some important implications, demonstrating the desirability of use of a method for the slow, extended release of rhGGF2 within the nerve guide tube.

We claim:

1. A device comprising a microporous underlayment with microcapillary pores wherein said pores are coated but not completely filled by a microskin to which a biologically active macromolecular agent is bound.

2. A device comprising a microporous underlayment with microcapillary pores wherein said pores are coated but not completely filled by a microskin to which a biologically active macromolecular agent is bound and is releasable therefrom.

3. The device of claim 1 wherein said microporous underlayment comprises a polymer.

4. The device of claim 3 wherein said polymer comprises one or more monomers selected from the group consisting of an olefin, amide, carbonate, ester, styrene, sulphone, imide, vinyl chloride, aldehyde, arylate, haloolefin acetyl, acrylate, urethane, vinylidine fluoride, vinylidine chloride, cellulose esters or cellulose, lactide, anhydride, glycolide, saccharide and amino acids.

5. The device of claim 1 wherein said microskin comprises a substance capable of binding to said underlayment and binding said macromolecule in a manner enabling subsequent controlled release of said biologically active macromolecular agent.

6. The device of claim 5 wherein said microskin comprises one or more substances selected from the group consisting of collagens, fibronectins, laminins, proteoglycans, glycolipids and glycosaminoglycans.

7. The device of claim 5 wherein said microskin comprises a synthetic polymer of one or more monomers selected from the group of olefin, amide, carbonate, ester, styrene, sulphone, imide, vinyl chloride, aldehyde, arylate, haloolefin acetyl, acrylate, urethane, vinylidene fluoride, vinylidene chloride, cellulose esters, lactide, anhydride, glycolide, saccharide and amino acids.

8. The device of claim 1 wherein said biologically active macromolecular agent is comprised of amino acids or amino acid derivatives.

9. The device of claim 1 wherein said biologically active macromolecular agent binds to said microskin by cooperative non-covalent binding.

10. The device of claim 1 wherein said underlayment, said microskin and said biologically active macromolecular agent are biodegradable.

11. The device of claim 1 wherein said device is of a size and shape suitable for placement in an environment of use.

12. The device of claim 11 wherein said shape is selected from the group consisting of cylindrical, bullet, elliptical, circular, bulbous, loop, bow, ellipsoid, hollow cylindrical, rectangular, doughnut and crescent.

13. A device comprising a microporous underlayment with microcapillary pores comprised of cellulose, wherein said pores are coated but not completely filled by a microskin comprised of collagen to which glial growth factor 2 is bound and is releasable therefrom.

14. A method for controlled delivery of a biologically active macromolecular agent comprising placement of the device of claim 1 in an environment of use.

15. The method of claim 14 wherein said environment of use is a mammalian body.

16. A method of treatment or therapy for a subject with a disorder or susceptibility to a disorder comprising placement of the device of claim 1 in said subject.

17. The method of claim 16 wherein said placement of the device is proximate to a therapeutic target within said subject for said treatment or therapy.

18. The method of claim 16 wherein said disorder comprises traumatic injury.

19. A method of treatment or therapy involving nerve regeneration for a human disorder comprising placement of the device of claim 13 proximate to a site of said nerve regeneration.

20. A method for making the device of claim 1 comprising the steps of:
   a) fabricating the microporous underlayment with microcapillary pores;
   b) coating but not completely filling said pores of the microporous underlayment with a microskin; and
   c) binding the biologically active macromolecular agent to the microskin.

* * * * *